United States Patent [19]
Wright et al.

[11] Patent Number: 5,322,699
[45] Date of Patent: Jun. 21, 1994

[54] LEUKOCYTE-DERIVED CR3 MODULATOR, INTEGRIN MODULATING FACTOR-1 (IMF-1)

[75] Inventors: Samuel D. Wright; Anne Hermanowski-Vosatka, both of New York, N.Y.

[73] Assignee: The Rockefeller University, New York, N.Y.

[21] Appl. No.: 650,062

[22] Filed: Feb. 4, 1991

[51] Int. Cl.$^5$ .................. A61K 35/14; A61K 37/22
[52] U.S. Cl. .................. 424/534; 424/115; 530/395; 435/7.24
[58] Field of Search .............. 424/115, 534; 435/240.2; 530/350, 395

[56] References Cited

U.S. PATENT DOCUMENTS

| | | | |
|---|---|---|---|
| 4,684,623 | 8/1987 | Larrick et al. | 514/12 |
| 4,686,100 | 8/1987 | Raffin et al. | 424/85 |
| 4,794,277 | 1/1989 | Arford et al. | 424/85.8 |
| 4,840,793 | 6/1989 | Todd, III et al. | 424/85.8 |
| 4,935,234 | 6/1990 | Todd, III et al. | 424/85.8 |

FOREIGN PATENT DOCUMENTS

WO88/06592 9/1988 PCT Int'l Appl. .......... C07H 21/04

OTHER PUBLICATIONS

Rosso et al., J. Exp. Pathol. 3(1):425-7 (1989).
Smyth et al., J. Biol. Chem. 267:15568-77 (1992).
Wright et al., J. Immunol. 136:1759-64 (1986).
Schleiffenbaum et al., J. Immunol. 142:3537-45 (1989).
Philips et al., J. Clin. Invest. 82:495-501 (1988).
Dransfield, Chem. Immunol. 50:13-33 (1991).
Hermanowski-Vosatka, A., et al. (1992) Cell 68:341-52.
Lehninger, A. L., Biochemistry, 2nd ed., pp. 379-380. New York: Worth, 1975.
Wright et al., Proc. Natl. Acad. Sci. USA, 80, pp. 5699-5703 (1983).
Tuomanen et al., J. Infect. Dis., 151, pp. 535-540 (1985).
Quagliarello et al., J. Clin. Invest., 77, pp. 1084-1095 (1986).
Arfors et al., Blood, 69, pp. 338-340 (1987).
Ismail et al., Blood, 69, pp. 1167-1174 (1987).
Price et al., J. Immunology, 139, pp. 4174-4177 (1987).
Quazliarello et al., Abstracts of the 1987 ICAAC, p. 204 (1987).
Rosen et al., J. Exp. Med., 166, pp. 1685-1701 (1987).
Sande et al., Ped. Infec. Dis. J., 6, pp. 1143-1171 (1987).
Tuomanen et al., J. Infect. Dis., 155, pp. 985-990 (1987).
Tuomanen et al., Am. Rev. Respir. Dis., 135, pp. 869-874 (1987).
Ripley-Petzoldt et al., J. Infect. Dis., 157, pp. 245-255 (1988).
Simpson et al., J. Clin. Invest., 81, pp. 624-629 (1988).
Tauber et al., J. Infect. Dis., 157, pp. 456-464 (1988).
Wright et al., Proc. Natl. Acad. Sci. USA, 85, pp. 7734-7738 (1988).
Lo et al., J. Exp. Med., 169, pp. 1779-1793 (1989).
Tuomanen et al., J. Exp. Med., 170, pp. 959-968 (1989).
Tuomanen et al., Ped. Inf. Dis. J., 8(12), pp. 924-928 (1989).
Fischer et al., Lancet, Nov. 8, pp. 1058-1061 (1986).
Honn, K., et al., "Lipoxygenase Products Regulate IRGpllb/lla Receptor Mediated Adhesion Of Tumor Cells To Endothelial Cells, Subendothelial Matrix And Fibronectin", Proc. Soc. Exp. Biol. Med., 189:130-135 (1988).
Hass, Thomas A., et al., "Binding Of 13-Hode and 5-, 12- and 15-Hete To Endothelial Cells And Subsequent Platelet, Neutrophil And Tumor Cell Adhesion", Biochimica et Biophysica Acta., 961:153-159 (1988).

Primary Examiner—Robert J. Hill, Jr.
Assistant Examiner—David L. Fitzgerald
Attorney, Agent, or Firm—Klauber & Jackson

[57] ABSTRACT

The invention is concerned with the discovery, isolation and purification of an agent or factor named herein the CR3 modulator or CMF-1 that is synthesized by polymorphonuclear leukocytes (PMN) in response to agonists which enhance CD18 activity. The CR3 modulator binds to CD18 and activates its adhesion-promoting ability. The CR3 modulator appears to be transiently produced by PMN as an acidic amphiphilic lipid. The CR3 modulator can be assayed by adding dilutions of a CR3 modulator -containing solution to resting PMN and observing the ability of CR3 to mediate binding of erythrocytes coated with C3bi (EC3bi). The isolation of the CR3 modulator, its biological and physical properties and diagnostic and therapeutic uses are described.

16 Claims, 17 Drawing Sheets

CMF PURIFICATION PROCEDURE harvest $10^9$-$10^{10}$ PMN, treat with agonist
↓
extract 3X in CMW 10:10:1
sonicate; stir for total 36 hrs or more
↓
pool supernatants from cell pellet extraction
↓
DEAE sephadex
load sample in organic
elute acidic lipids in 0.065 M salt
↓
desalt with $C_{18}$ Sep Pak cartridge
↓
*[optional]*
Folch cut: 4:1 organic:aqueous
org: CM 2:1
aq: 0.01 M NaCl
↓
partially purified
lipid extract

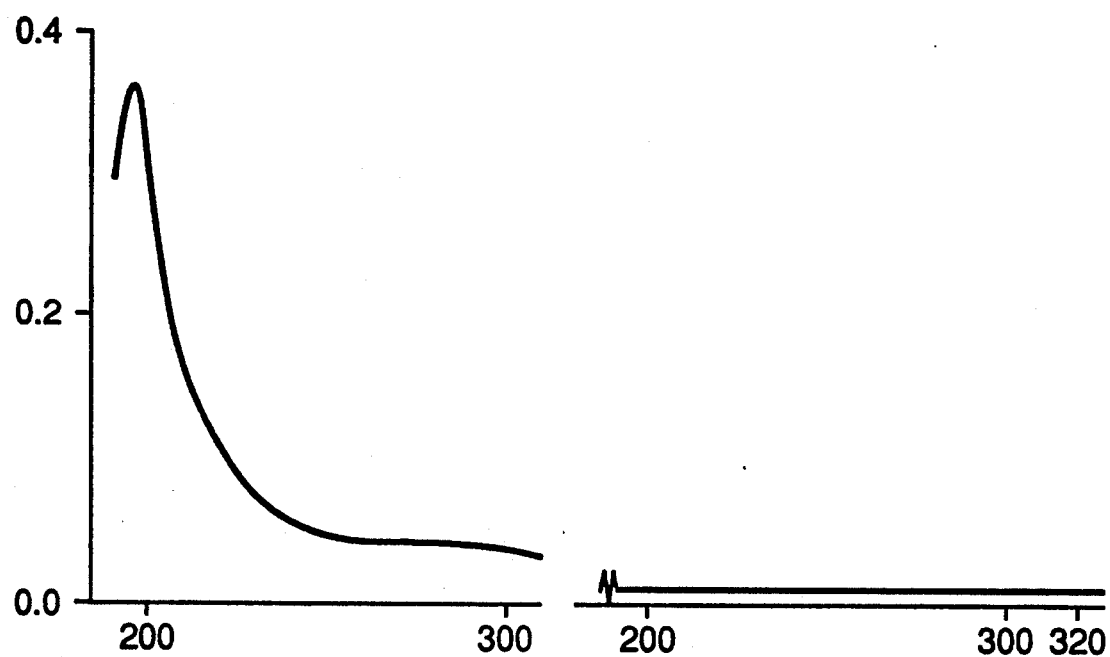
F I G. 14

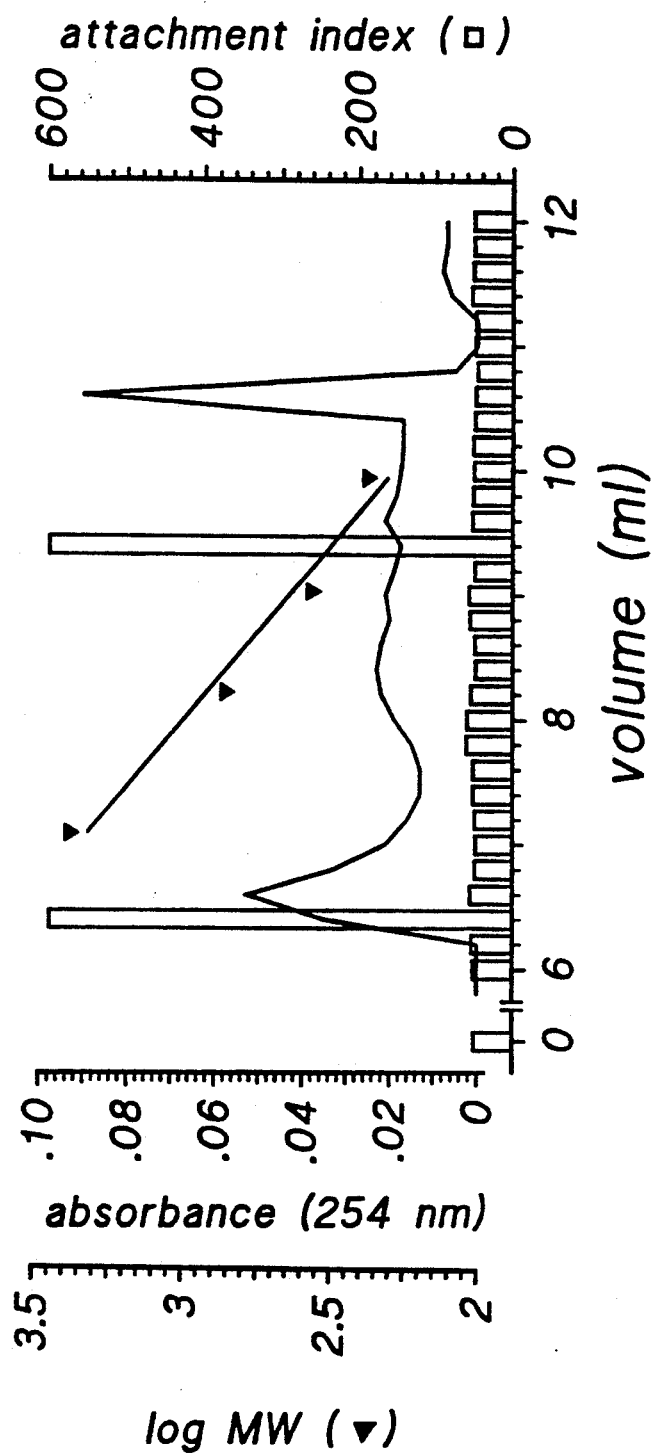
F I G. 16

LEUKOCYTE-DERIVED CR3 MODULATOR, INTEGRIN MODULATING FACTOR-1 (IMF-1)

This invention was made with Government support under AI 22003 and AI 24775 awarded by the National Institutes of Health. The Government has certain rights in this invention.

TECHNICAL FIELD OF THE INVENTION

The present invention relates generally to inflammation and, more particularly, to the activity and related mechanisms surrounding the migration of leukocytes in response to infectious agents and related invasive stimuli.

BACKGROUND OF THE INVENTION

Inflammatory diseases are characterized by movement of leukocytes into affected tissues. Once there, cells such as polymorphonuclear leukocytes (PMN) are thought to cause tissue damage directly through the release of lytic enzymes and reactive small molecules such as superoxide anion, and indirectly by release of inflammatory mediators. Depletion of PMN from the circulation of animals minimizes tissue damage in several inflammatory settings.

The CD18 antigens are a family of three heterodimeric receptors sharing a common $\beta$ chain, CD18, and homologous but distinct $\alpha$ chains, CD11a, CD11b and CD11c. These receptors are expressed on all leukocytes, and are members of the integrin superfamily (R. O. Hynes, 1987). Integrins are $\alpha_1\beta_1$ heterodimers that require divalent cations and warm temperatures for ligand binding (Hynes, Supra.) and mediate cell-cell and cell-extracellular matrix adhesion interactions. Many of the ligands are bound via a tripeptide sequence, Arg-Gly-Asp, or RGD. The leukocyte integrins (B$_2$ integrins or CD18 antigens) participate in adhesion of cells by recognizing a variety of surface bound ligands including ICAM-1, ICAM-2, C3bi, fibrinogen and unidentified structures on endothelium (S. D. Wright et al., 1990).

One of the CD18 antigens, complement receptor type 3 (CR3, also known as CD11b/CD18), is found on human polymorphonuclear leukocytes (PMN), monocytes and macrophages. Ligands for this receptor include C3bi, a cleavage product of the third component of complement, fibrinogen, and an as yet uncharacterized molecule on endothelial cells (S. D. Wright et al., Supra.). A second type of ligand is the lipid IVa portion of lipopolysaccharide from gram-negative bacteria (S. D. Wright et al., 1986; S. D. Wright et al., 1989) which binds at a site on the receptor that can be distinguished from that for the proteinaceous ligands by blockade with distinct monoclonal antibodies.

Movement of PMN into tissues can be dramatically reduced by blocking CD18 antigens with monoclonal antibodies. Such blockade has been found to prevent PMN migration into the peritoneal cavity, brain, heart, bowel and skin and has been shown to reduce tissue injury in models of meningitis, cardiac and bowel ischemia and reperfusion injury and hemorrhagic shock (E. I. Tuomanen et al., 1989; P. J. Simpson et al., 1988; N. B. Vedder et al., 1988; L. A. Hernandez et al., 1987). This course of therapy has been suggested in U.S. Patent No. 4,797,277 to Arfors with respect to reperfusion injury, and in European Patent Application No. 0 346 078 A2 published 13 December, 1989, With regard to a variety of inflammatory conditions related to PMN migration.

In both publications, certain antibodies were identified and postulated to block the CD18 receptor and consequently, the migration and adhesion of PMN to endothelium. The structure and origin of these antibodies, however, did not suggest an endogenous intracellular mechanism to account for the restriction of CD18 function to sites of inflammation.

The capacity of the CD18 molecule to bind endothelium (or any of its ligands) may be rapidly turned on and off. This enables leukocytes to rapidly adhere to endothelium upon stimulation by chemoattractants, and further allows cells to locomote by adhering at their leading edge and releasing adhesion at the uropod. This regulated behavior enables CD18 to promote movement of leukocytes into tissues.

CR3 on human PMN binds its ligands in a regulated manner. This property was first described by Wright and Meyer (S. D. Wright et al., 1986) using a rosetting assay. PMN are first allowed to adhere to a culture well, and sheep erythrocytes bearing covalently attached C3bi on their surface (EC3bi) are then added. After a brief incubation, unbound E are washed away and the number of E bound per 100 PMN is scored by phase contrast microscopy (the attachment index). Visually, the smaller E form a rosette-like arrangement when attached to PMN.

CR3 on resting PMN binds poorly to its ligand, C3bi; however, when the PMN are treated with agonists such as phorbol myristate acetate (PMA), the binding activity of CR3 transiently increases. After 20 minutes in PMA, rosetting rises by 5–10 fold, but by 60 minutes in PMA the rosetting declines below starting levels. The change in binding of C3bi is only partially explained by the observed 2–3 fold increase in surface receptor numbers that are released from specific granules. Receptor expression remains high after degranulation, even though binding falls back down below baseline.

In addition, studies (S.K. Lo et al., 1989) show CD18 activity is enhanced after phorbol ester stimulation of PMN-derived cytoplasts, which lack specific granules and therefore have no means of increasing receptor numbers at the plasma membrane. Therefore, some other means of regulation is involved in the transient changes in binding. Detmers et al. (1987) have shown that enhanced receptor binding correlates with the localization of receptor in small clusters on the cell surface. However, the mechanism of such clustering is unknown, as is any effect on the $K_d$ of individual receptors in the cluster, and it is toward the elucidation of these phenomena that the present invention is generally directed.

SUMMARY OF THE INVENTION

In accordance with the present invention, an agent or factor has been discovered, isolated and purified, that is synthesized by polymorphonuclear leukocytes in response to agonists which enhance CD18 activity. The factor is alternately and variously referred to hereinafter as the CR3 modulator, CR3 modulating factor or CMF-1. The CR3 modulator has thus far been identified as to certain of its physical and functional characteristics. At present, the CR3 modulator is known to possess the following physical characteristics:

(A) It is an acidic amphiphilic lipid or lipid-like compound that is synthesized by stimulated polymorphonuclear leukocytes;

(B) It possesses a molecular weight of about 340 daltons; and (C) It retains its activity even after treatment with known bases such as sodium hydroxide and ammonium hydroxide;

(D) It appears to derive from a biosynthetic product of mevalonate synthesis and is possibly isoprenoid in structure.

In addition to the physical characteristics identified above, the CR3 modulator of the invention demonstrates the following activities:

(A) It binds directly to CD18;

(B) It activates the adhesion-promoting activity of CD18;

(C) It increases CR3 binding at the binding site for C3bi;

(D) It increases PMN binding to endothelial cells, fibrinogen-coated substrates and lipid IVa-coated substrates;

(E) It increases LFA-1-mediated lymphocyte adhesion;

(F) It can restimulate PMN that have been previously activated with an activator such as PMA; and (G) Its activity is dose-dependent.

The CR3 modulator is also characterized by the activities that it does not possess. Specifically, the CR3 modulator does not induce the production of tumor necrosis factor (TNF) by whole blood, and likewise does not cause degranulation of PMN. As a consequence of this latter characteristic, it has been inferred that the CR3 modulator does not appear to act as a general agonist for PMN, but appears rather to be specific in its activity to CR3.

The CR3 modulator of the present invention may be prepared by isolation and purification from polymorphonuclear leukocytes. The PMN or active fragments likely to have the CR3 modulator associated therewith may be subjected to a series of known isolation techniques, such as for example, immunoprecipitation with the CD18, whereupon the CR3 modulator may be recovered. The present invention naturally contemplates alternate means for preparation of the CR3 modulator, including stimulation of PMN with promoters of CR3 modulator synthesis followed by the isolation and recovery of the CR3 modulator as indicated above, as well as chemical synthesis, and the invention is accordingly intended to cover such alternate preparations within its scope.

The invention further includes a method for detecting idiopathic or invasive stimuli on the basis of their ability to elicit the production and activities affected by the CR3 modulator. In particular, invasive stimuli could be identified and detected by their ability to stimulate the production of the CR3 modulator by polymorphonuclear cells. For example, in this method, samples of polymorphonuclear cells could be treated with/exposed to a number of known stimulator materials such as endotoxin, trypanosomes or the like, as a control, while parallel cellular samples could be treated with or exposed to an extract of material from the situs of the presumed infective stimulus. All samples could then be incubated, and thereafter, in one embodiment, samples could be assayed for the presence of the CR3 modulator. Alternately, aliquots of the incubated samples could be added to samples of erythrocytes coated with C3bi (EC3bi) to determine whether PMN binding of the erythrocytes takes place.

In similar fashion, an assay system for screening of potential drugs effective to counteract the CR3 modulator or to prevent its synthesis may be prepared. For example, the test drug could be administered to a PMN sample cell with the CR3 modulator and a sample of cells to which activated PMN are known to bind, such as EC3bi, to determine its effect upon the binding activity of the PMN. Alternatively, the test drug could be administered to a PMN sample colony with an agonist that normally includes CR3 modulator production. Measurement of the CR3 modulator in the sample will determine if the test drug blocks CR3 modulator production.

The present invention also relates to a method for detecting the presence of stimulated, spontaneous, or idiopathic pathological states in mammals, by measuring the activity of PMN as a function of the presence of the CR3 modulator of the present invention. More particularly, the activity of the CR3 modulator may be followed directly by the assay techniques discussed later on, through the use of an appropriately labeled quantity of the CR3 modulator. Alternately, the CR3 modulator can be used to raise binding partners or antagonists that could in turn, be labeled and introduced into a medium to test for the presence and amount of CR3 modulator therein, and to thereby assess the state of the host from which the medium was drawn.

Thus, both the CR3 modulator and any antagonists that may be prepared thereagainst, are capable of use in connection with various diagnostic techniques, including immunoassays, such as a radioimmunoassay, using for example, an antagonist to the CR3 modulator that has been labeled by either radioactive addition, reduction with sodium borohydride, or radioiodination.

In an immunoassay, a control quantity of the CR3 modulator, its antagonist, or the like may be prepared and labeled with an enzyme, a specific binding partner and/or a radioactive element, and may then be introduced into a blood sample of a mammal believed to be undergoing invasion. After the labeled material or its binding partner(s) has had an opportunity to react with sites within the sample, the resulting mass may be examined by known techniques, which may vary with the nature of the label attached.

In the instance where a radioactive label, such as the isotopes $^{14}C$, $^{131}I$, $^{3}H$, $^{125}I$ and $^{35}S$ are used, known currently available counting procedures may be utilized. In the instance where the label is an enzyme, detection may be accomplished by any of the presently utilized colorimetric, spectrophotometric, fluorospectro-photometric or gasometric techniques known in the art.

The present invention includes an assay system which may be prepared in the form of a test kit for the quantitative analysis of the extent of the presence of the CR3 modulator. The system or test kit may comprise a labeled component prepared by one of the radioactive and/or enzymatic techniques discussed herein, coupling a label to the CR3 modulator; and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the CR3 modulator, antagonists to the CR3 modulator, or upon agents or other drugs determined to possess the same or an antagonistic activity. A first therapeutic protocol is associated with the prevention of the manifestations of conditions following from the binding activity of the CR3 modulator, such as inflammation, and comprises administering either an antagonist to the CR3 modulator or an agent capable of modulating the production and/or activity of the CR3 modulator, either individually or in mixture with each other in an amount effective to prevent the development of those conditions in the host.

The method of inhibiting the synthesis of the CR3 modulator contemplates blocking the reaction/interaction between PMN or any active fragments thereof and the promoters of CR3 modulator synthesis. Accordingly, this embodiment of the method is directed toward the inhibition of agents that serve as CR3 modulator synthesis promoters, such as the agonists that react with receptors on polymorphonuclear leukocytes, intracellular signaling agents that initiate CR3 modulator synthesis, enzymes that synthesize the CR3 modulator, and agents that promote or participate in the synthesis or production of molecules that serve as metabolic precursors to the CR3 modulator. The method therefore comprises introducing to a medium or other sample or substrate, antagonists or antibodies to the aforementioned agents, in amounts effective to block or inhibit the synthesis of the CR3 modulator. Representative agents that promote CR3 modulator synthesis include phorbol myristate acetate (PMA); platelet activating factor (PAF); tumor necrosis factor (TNF); formyl-NorLeu-Leu-Phe (fNLLP); interleukin-8 (IL-8) and C5a. Representative intracellular signaling agents are selected from protein kinase C, cGMP, G-proteins and mixtures. Suitable antagonists/antibodies to the promoters of CR3 modulator synthesis may be determined by appropriate assays.

The first aspect of the therapeutic method generally referred to above includes a method for the treatment of inflammation resulting from infection, injuries, immunologically unknown causes by the administration of pharmaceutical compositions that may comprise effective quantities of antagonists to the CR3 modulator, antagonists to promoters of CR3 modulator synthesis, or other equally effective drugs developed for instance by a drug screening assay prepared and used in accordance with a further aspect of the present invention.

A variant embodiment of this therapeutic method could include initially detecting the presence and activity of the CR3 modulator and thereafter administering the appropriate pharmaceutical composition.

The present invention correspondingly extends to a method and associated agents and compositions for inhibiting the influx of leukocytes into the lung and other organs during sepsis or other infectious or non-infectious trauma, the method comprising administering a therapeutic amount of an agent or composition comprising an antagonist to the CR3 modulator and/or antagonists to promoters of CR3 modulator synthesis. Additionally, this invention concerns a method and associated materials for inhibiting the ingress of leukocytes into the lung or other organs in patients having endotoxic shock or adult respiratory distress syndrome of any cause by administration of a therapeutic amount of an antagonist to the CR3 modulator and/or an antagonist to promoters of CR3 modulator synthesis, to a patient in need of such therapy.

The invention also concerns a method and associated materials including pharmaceutical compositions for eliminating or reducing inflammation in a patient wherein the patient is being administered an anti-infective agent for an infectious disease which comprises the administration prior to, along with or after the anti-infective agent of a therapeutic amount of an antagonist to the CR3 modulator and/or an antagonist to promoters of CR3 modulator synthesis. Dosage forms combining an anti-infective agent and a therapeutic amount of the CR3 modulator antagonist and/or CR3 modulator synthesis antagonist thereof are also described.

A second therapeutic protocol in accordance with the present invention is predicated on the activation and mobilization of polymorphonuclear leukocytes to treat infection in instances where the host exhibits immune incapacity or dysfunction related to PMN inaction. In such instances, appropriate compositions containing the CR3 modulator or agents or drugs that mimic its activity could be administered to the patient or host in need of such treatment. The method of administration would include those known procedures, including parenteral techniques as are conventionally used by skilled medical personnel. Dosages and protocol of administration would likewise vary.

Accordingly, a principal object of the present invention is to provide a modulator of polymorphonuclear leukocyte activity in isolated and purified form that is synthesized by polymorphonuclear leukocytes in response to agonists which enhance CD18 activity.

It is a further object of the present invention to provide a method for the synthesis of a modulator as aforesaid (a CR3 modulator) by the stimulation of polymorphonuclear leukocytes.

It is a still further object of the present invention to provide a modulator as aforesaid (a CR3 modulator) that binds directly to the receptor CD18.

It is a still further object of the present invention to provide antagonists to the CR3 modulator as aforesaid, and methods for their preparation.

It is a still further object of the present invention to provide antagonists to the synthesis of the CR3 modulator as aforesaid, and methods for their preparation.

It is a further object of the present invention to provide methods for the preparation of the CR3 modulator, including, where appropriate, recombinant means.

It is a further object of the present invention to provide a method for detecting the presence of the CR3 modulator in mammals in which invasive, spontaneous, or idiopathic pathological states such as infection are suspected to be present.

It is a further object of the present invention to provide a method and associated assay system for screening substances such as drugs, agents and the like, potentially effective in either mimicking the activity or combating the adverse effects of the CR3 modulator in mammals.

It is a still further object of the present invention to provide a method for the treatment of mammals to control the amount or activity of the CR3 modulator, so as to alter the adverse consequences of such presence or activity.

It is a still further object of the present invention to provide a method for the treatment of mammals to promote the amount or activity of the CR3 modulator, so as to treat or avert the adverse consequences of invasive, spontaneous or idiopathic pathological states.

It is a still further object of the present invention to provide pharmaceutical compositions for use in therapeutic methods which comprise or are based upon the CR3 modulator or its binding partner(s), or upon agents or drugs that control the production, or that mimic or antagonize the activities of the CR3 modulator.

Other objects and advantages will become apparent to those skilled in the art from a review of the ensuing description which proceeds with reference to the following illustrative drawings.

BRIEF DESCRIPTION OF THE DRAWINGS

FIG. 1 shows a method for extracting partially purified CMF-1 from stimulated neutrophils. A pellet of stimulated PMN was treated with organic solvents, and the supernatants were dried down under vacuum in a rotary evaporator. A DEAE column of 2-20 ml in volume was used for starting material from $10^9$-$10^{10}$ cells, respectively. The dried extract was resuspended in 3 bed volumes of chloroform:methanol:water=30:60:8, and passed through the column. The column was then washed with 6 bed volumes of solvent and eluted with chloroform: methanol:0.8M sodium acetate=30:60:8. The eluate was dried down under vacuum and resuspended in distilled water. A Sep-Pak $C_{18}$ cartridge or a hand-packed column of the Sep-Pak sorbent was used for desalting material from $10^9$-$10^{10}$ cells, respectively. The $C_{18}$ a column was prewashed in methanol, chloroform:methanol=2:1, and methanol:1.6M sodium acetate=1:1 before sample was applied in at least 3 bed volumes of water. Salt was then washed out by extensive rinsing of the column with water (>6 bed volumes) and the lipid extract was eluted with methanol and chloroform:methanol=1:1. The eluted material may additionally be put through a Folch partitioning step, where it is separated to the saline upper phase in equilibrium with a lower phase of chloroform:methanol=2:1 before drying down and resuspending the material, for storage as a stock of partially purified CMF-1.

FIG. 14 is an ultraviolet spectrograph of CMF-1. A Perkin-Elmer Lambda 5 UV/Vis Spectrophotometer, equipped with a double beam and matched quartz cuvettes, was zeroed with acetonitrile in both cells (at right) and then CMF-1 purified by reverse phase chromatography (52,000 u/ml in acetonitrile) was added to one cell and a spectrum obtained (at left).

FIG. 16 is a graph demonstrating that CMF-1 has a molecular weight of 340±16 daltons. CMF-1 was loaded on a TSK G2000HXL size exclusion chromatography column and eluted in an isocratic gradient of tetrahydrofuran. Absorbance at 254 nm of the eluted material is indicated by the column profile. Elution volumes of molecular weight standards in the range of 1000-180 daltons are shown (triangles). Linear regression yielded a standard curve of y=−1.278x+3.302 with r$^2$=0.9884. CMF-1 activity (histogram) of each fraction was determined by rosetting assay.

DETAILED DESCRIPTION OF THE INVENTION

Figure 2:
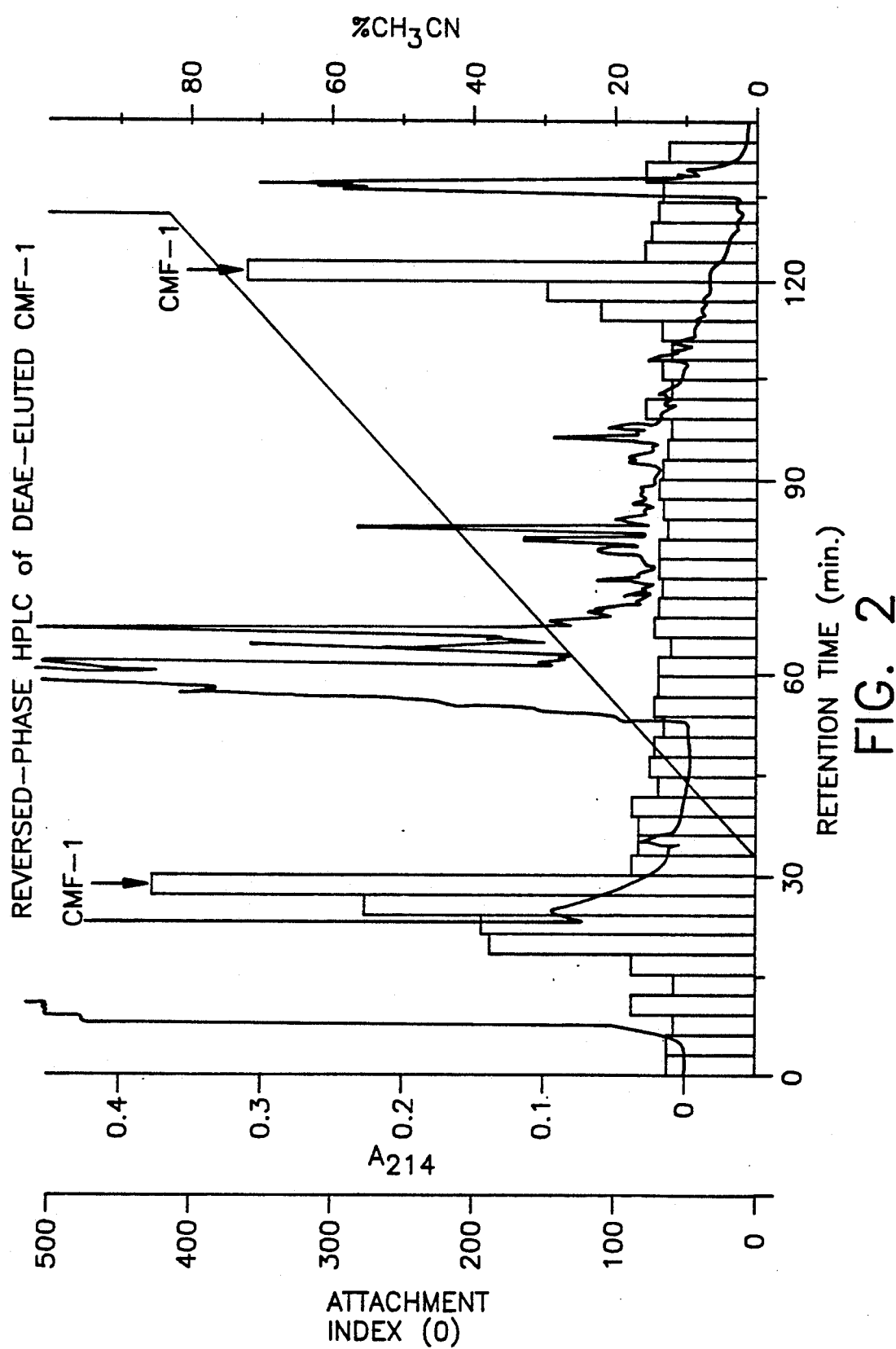
FIG. 2 is a typical run of partially purified lipid extract on a semi-preparative $C_{18}$ a HPLC column. Partially purified CMF-1 was loaded on a Versa-Pak $C_{18}$ reverse phase column (10 μm packing, 250 mm×10 mm) in distilled water. CMF-1 was eluted by a 1% per minute gradient from water to acetonitrile. CMF 1 (as measured by activity in rosetting assay, histogram) eluted at about 55% acetonitrile. CMF-1 activity was also present in the flowthrough, due to the presence of micelles containing CMF-1, which are hydrophilic and thus not retained by the column matrix. Loading with lower concentrations of material eliminated the breakthrough. The absence of absorbance at 214 nm in the active fractions was noted.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

An "agonist" is a chemical agent, compound, antigen or like material that mimics or promotes certain activity of a cellular colony, antigen, antibody, or other moiety, while an "antagonist" is an agent, compound, antibody or like material that counteracts, inhibits or blocks such activity.

An "antibody" is any immunoglobulin, including antibodies and fragments thereof, that binds a specific epitope. The term encompasses, inter alia, polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(V), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. (The disclosures of the art cited herein are hereby incorporated by reference). Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. Where present, an antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "substantially simultaneously" is used herein to mean within a time period sufficient to produce concurrent results; e.g., bacterial lysis as a result of antibiotic administration and amelioration or prevention of symptoms of inflammation that may occur as a result of that lysis by administration of an antagonist of CR3 modulator activity and/or synthesis, as described herein.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the movement of leukocytes to a site of inflammation.

In its initial aspect, the present invention concerns the isolation, purification and identification of an agent or factor that is synthesized by polymorphonuclear leukocytes (PMN) in response to agonists that enhance the activity of the CD18 receptor, and that stimulates a receptor on PMN known as complement receptor type 3 (CR3) or (CD11b/CD18). The activity of PMN as discussed earlier, and in particular their migration and binding to endothelial cells and other agents, appears to be activated by direct interaction with the present CR3 modulator. Thus, the understanding and corresponding control of the presence and activity of this factor carries with it significant corresponding implications in treatment of inflammation, on the one hand, and treatment of immune response dysfunction associated with PMN quiescence. Likewise, numerous diagnostic utilities are similarly foreseen.

The CR3 modulator of the present invention presently is determined to possess the following physical characteristics:
(A) It is an acidic amphiphilic lipid or lipid-like compound that is synthesized by stimulated polymorphonuclear leukocytes (PMN);
(B) It possesses a molecular weight of about 340 daltons; and
(C) It retains its activity even after treatment with known bases such as sodium hydroxide and ammonium hydroxide;
(D) It appears to derive from a biosynthetic product of mevalonate synthesis and is possibly isoprenoid in structure.

The CR3 modulator of the invention is also distinctive in its activity profile. Thus, the CR3 modulator exhibits the following activities as presently determined:
(A) It binds directly to CD18;
(B) It activates the adhesion-promoting activity of CD18;
(C) It increases CR3 binding at the binding site for C3bi;
(D) It increases PMN binding to endothelial cells, fibrinogen-coated substrates and lipid IVa-coated substrates;
(E) It increases LFA-1 -mediated lymphocyte adhesion;
(F) It can restimulate PMN that have been previously activated with an activator such as PMA; and
(G) Its activity is dose-dependent In addition to those activities that the present CR3 modulator possesses, it is also distinctive in those activities that it appears to lack. Specifically, the CR3 modulator does not induce the production of tumor necrosis factor (TNF) by whole blood, and likewise does not cause degranulation of PMN while it is active. As such, with respect to this latter characteristic, it is determined that the CR3 modulator does not appear to act as a general agonist for PMN, but appears rather to be specific in its activity to CR3.

As described earlier, the CR3 modulator may be prepared by recovery and purification from PMN. The PMN or active fragments likely to have the CR3 modulator associated therewith may be subjected to known isolation techniques to effect recovery. Alternately, the CR3 modulator is capable of industrial synthesis from chemical reagents and starting materials, and the invention is intended to include such procedures within its scope.

As discussed earlier, the CR3 modulator, its analogs, binding partner(s) or other ligands or agents exhibiting either mimicry or antagonism to the CR3 modulator or control over its production, may be prepared in pharmaceutical compositions, with a suitable carrier and at a strength effective for administration by various means to a patient having a tissue infection or other pathological derangement such as immune system dysfunction involving leukocytes, for the treatment thereof. A variety of administrative techniques may be utilized, among them topical applications as in ointments or on surgical and other topical appliances such as, surgical sponges, bandages, gauze pads, and the like. Also, such compositions may be administered by parenteral techniques such as subcutaneous, intravenous and intraperitoneal injections, including delivery in an irrigation fluid used to wash body wound areas, catheterizations and the like. Average quantities of the CR3 modulator may vary and in particular should be based upon the recommendations and prescription of a qualified physician or veterinarian.

Representative therapeutic compositions useful in practicing the therapeutic methods of this invention may include, in admixture, a pharmaceutically acceptable excipient (carrier) and one or more of a CR3 modulator/modulator synthesis promoter antagonist, or analog thereof, as described herein as an active ingredient. Preferred therapeutic compositions further include an effective amount of the CR3 modulator/modulator synthesis promoter antagonist or analog thereof, and one or more of the following active ingredients: an antibiotic, a steroid. Exemplary formulations are given below:

FORMULATIONS

| Ingredient | Formulations mg/ml |
|---|---|
| Intravenous Formulation I | |
| cefotaxime | 250.0 |
| CR3 modulator antagonist | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| ampicillin | 250.0 |
| CR3 modulator antagonist | 10.0 |
| sodium bisulfite USP | 3.2 |
| disodium edetate USP | 0.1 |
| water for injection q.s.a.d. | 1.0 ml |
| Intravenous Formulation III | |
| gentamicin (charged as sulfate) | 40.0 |
| CR3 modulator antagonist | 10.0 |
| sodium bisulfite USP | 3.2 |
| disodium edetate USP | 0.1 |
| water for injection q.s.a.d. | 1.0 ml |
| Intravenous Formulation IV | |
| CR3 modulator antagonist | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation V | |
| CR3 modulator antagonist | 10.0 |
| sodium bisulfite USP | 3.2 |
| disodium edetate USP | 0.1 |
| water for injection q.s.a.d. | 1.0 ml |

Corresponding therapeutic methods are contemplated herein, and accordingly the present invention extends to a method of inhibiting the influx of leukocytes into the lung and other organs during sepsis or other non-infectious trauma which comprises the administration of a therapeutic amount of an antagonist to the CR3 modulator and particularly a pharmaceutical composition thereof to a patient in need of such therapy.

The inflammation to be treated by the therapeutic method of the present invention may result from any of a variety of infective agents, including gram-positive and gram-negative bacteria as well as viruses, parasites and fungi, or may arise from a non-infectious source such as trauma. Particularly targeted infections are those which are susceptible to treatment with beta-lactam antibiotics, such as *Haemophilus influenzae* B; *N. meningitides* b; pneumococci, *Streptococcus pneumoniae; Escherichia coli: Staphylococcus epidermidus: Staphylococcus aureus*; group B Streptococci; Salmonella; *Bacillus subtillis*; and *Pseudomonas aeruqinosa*.

The inflamed organ which is the target of the therapeutic method of the invention can likewise be any body organ susceptible to inflammation by the above-described agents. The present invention is, however, particularly adaptable to the treatment of the lung, central nervous system, kidney, joints, endocardium, eyes and ears, with the treatment of the lung being a highly preferred embodiment.

The therapeutic method of the present invention may be useful in preventing the ingress of leukocytes into the lung of mammals afflicted with sepsis. Such activity enables their preferred route of administration to be intravenous, and their administration to be particularly useful in the treatment of such infections, including those arising from pneumococci, *Haemoohilus influenzae* B, *N. meninoitides* b and *Escherichia coli,* group B Streptococcus, Staphylococci and Pseudomonas.

Similarly, the present invention is also applicable to inflammation arising from causes other than infections, such as that seen in stroke, mild cardioinfarction and other ischemia reperfusion injuries, ARDS precipitated by burns, surgery, toxic chemicals, fracture of bones, or other trauma.

CR3 modulator synthesis promoters are meant to include, but are not limited to, agents that block or antagonize the interaction of agonists with receptors on PMN, agents that block or antagonize the production of intracellular signals that initiate CR3 modulator synthesis, agents that block or antagonize the enzymes which synthesize the CR3 modulator, and agents that block or antagonize the production of molecules which serve as metabolic precursors of the CR3 modulator.

A further method of the present invention is that of reducing or eliminating the influx of leukocytes into the lung in endotoxic shock or adult respiratory distress syndrome associated with the administration of an anti-infective agent. The method comprises the administration prior to, along with, or after the anti-infective agent of a therapeutic amount of an antagonist to the CR3 modulator and/or the agents that promote its synthesis by PMN, or analogs thereof to a patient in need of such therapy. Due to the mechanism of their therapeutic activity, anti-infective agents, and particularly beta-lactam antibiotics, cause additional inflammation as a result of their therapeutic effect. Although such anti-infective agents sterilize a given infection, they cause release of toxic products, for example, the cell wall and/or endotoxin of the infecting agent. Such bacterial components initiate an inflammatory response, often most acute in the lung. It is this inflammation which contributes significantly to the lung damage that is the long-term consequence of many infections.

Reduction or elimination of inflammation in inflammatory diseases, particularly endotoxic shock and adult respiratory distress syndrome, results in a diminution of the organ damage that usually accompanies such disease states. Since the antagonists to the CR3 modulator may possess the unique ability to block movement of leukocytes into the lung and other organs by preventing the activation of CD18, they may be particularly well suited to treat both non-infectious causes and infectious causes.

Causative infective agents are those such as *Haemophilus influenza* B, *N. meninoitides* b, *E. coli, Staphylococci*, or a pneumococci such as *Streptococcus pneumoniae*. Such infections are generally treated with an aminoglycoside such as gentamicin or a beta-lactam antibiotic such as a penicillin or cephalosporin. Among the typically utilized aminoglycosides, penicillins and cephalosporins used in the treatment of such infections are cephalothin, cephaloridine, carbenicillin, ampicillin, nafcillin sodium, cloxacillin, dicloxacillin, oxacillin, methicillin sodium, phenoxymethyl penicillin, procaine penicillin G, benzathine penicillin G, penicillin G, cephacetrile sodium, cephalexin, cephapirin sodium, cephradine, penicillin V, gentamicin, kanamycin, chloramphenicol, cefotaxime, ceftriaxione, vancomycin, and imipenem.

Due to the ability of the antagonist to CR3 modulator/promoters of CR3 modulator synthesis to reduce or eliminate the influx of leukocytes into the lung and other organs in a infectious disease caused by the administration of an anti-infective agent, the antagonist to the CR3 modulator/promoters of CR3 modulator synthesis can be combined in a single unit dosage form with the anti-infective agent for convenience of administration. Such dosage form is most preferably an intravenous dosage form since most anti-infective agents, particularly the beta-lactam antibiotics, are available in a suitable chemical form for administration via the intravenous route. This is also the preferred route of administration for the antagonists of the present invention. Typically, the anti-infective agent and the antagonist can be combined in a single ampoule solution. Where this is not possible, the anti-infective agent and the antagonist can be packaged separately and mixed just prior to injection. Administration can likewise be via a mixture with any standard intravenous solution, i.e., normal saline.

The amount of anti-infective agent in the dosage form is dependent upon the particular anti-infective agent being utilized and the particular infection being treated. The amount of the antagonist utilized in a dosage form can range from about 1 to about 1,000 mg, with 10–100 mg per dosage unit being highly preferred. Dosages can be administered one to four times daily, with continued therapy for as long as the infection persists.

The method of administering the dosage unit may, of course, be varied by the treating physician due to patient condition and the severity of the infectious disease being treated.

As indicated earlier, the present invention is applicable to the treatment of a variety of inflammatory disease states including infectious diseases where active infection exists at any body site, such as in the instance of meningitis. Also included are conditions such as secondary infections that may occur at a site of antigen deposition that is secondary to a primary infection at a distant body site, and exemplary specific conditions would include meningitis, encephalitis, arthritis, uveitis, colitis, such as inflammatory bowel/Crohn's disease, and dermatitis such as psoriasis, whether acute or chronic. Also included is the inflammation that results from alterations in leukocyte movement during infection such as adult respiratory distress syndrome associated with sepsis.

Other inflammatory disease states deriving from immune disorders including involvement with T-cell and/or macrophage attachment/recognition, such as acute and delayed hypersensitivity, graft vs. host disease; primary auto-immune conditions such as pernicious anemia, and infection related auto-immune conditions such as Type I diabetes mellitus, and flares during rheumatoid arthritis for diseases that involve leukocyte diapedesis, such as multiple sclerosis; antigen-antibody complex mediated diseases including certain of the secondary infection states listed above; and transplant rejection. Inflammation due to toxic shock or trauma such as adult respiratory distress syndrome and reperfusion injury; and that which is due to tumorous conditions such as leukocyte dyscrasias and metastasis, is likewise included within the scope hereof.

In addition to the therapeutic methods that are based on the administration of an antagonist to the CR3 modulator, the invention extends to the achievement of the same therapeutic objectives by blocking the synthesis of the CR3 modulator. Thus, and as discussed earlier herein, the method of the present invention comprises the administration of antagonists, antibodies, or other agents that are able to block the action of CR3 modulator synthesis promoters. CR3 modulator synthesis promoters are meant to include, but are not limited to, agents that block or antagonize the interaction of agonists with receptors on PMN, agents that block or antagonize the production of intracellular signals that initiate CR3 modulator synthesis, agents that block or antagonize the enzymes which synthesize the CMF modulator, and agents that block or antagonize the production of molecules which serve as metabolic precursors of CR3 modulator. Representative agents that promote CR3 modulator synthesis include phorbol myristate acetate (PMA); platelet activating factor (PAF); tumor necrosis factor (TNF); formyl-NorLeu-Leu-Phe (fNLLP); interleukin-8 (IL-8) and C5a. Representative intracellular signaling agents are selected from protein kinase C, cGMP, G-proteins and mixtures. Suitable antagonists/antibodies to the promoters of CR3 modulator synthesis may be determined by appropriate assays; and the practice of the method includes the determination and/or development of appropriate antagonists or antibodies that may be formulated and administered in accordance with an acceptable therapeutic protocol.

The present invention also relates to a variety of diagnostic applications, including methods for detecting the presence of invasive stimuli by reference to their ability to elicit the activities which are affected by the present CR3 modulator. As mentioned earlier, the CR3 modulator can be used to produce binding partners to itself by a variety of known techniques, and such binding partners could then be utilized as in tests for the presence of the CR3 modulator in suspect mammalian hosts.

The presence of CR3 modulator activity in mammals can be ascertained by the usual immunological procedures applicable to such determinations. A number of useful procedures are known. Three such procedures which are especially useful utilize either the CR3 modulator or its antagonist or other binding partner labeled with a detectable label. The procedures may be summarized by the following equations wherein the asterisk indicates that the particle is labeled, and "Mod" stands for the CR3 modulator and "Ant" stands for binding partner to the CR3 modulator:

A. $Mod^* + Ant = Mod^*Ant$

B. $Mod + Ant^* = ModAnt^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance, the CR3 modulator forms complexes with binding partners and one member of the complex is labeled with a detectable label. The fact that a complex has formed and, if desired, the amount thereof, can be determined by known methods applicable to the detection of labels.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The CR3 modulator or its binding partner(s) can also be labeled with a radioactive element or with an enzyme. The radioactive label can be detected by any of the currently available counting procedures. The preferred isotope may be selected from $^{14}C$, $^{131}I$, $^{3}H$, $^{125}I$ and $^{35}S$.

Enzyme labels are likewise useful, and can be detected by any of the presently utilized colorimetric, spectrophotometric, fluorospectrophotometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, $\beta$-glucuronidase, $\beta$-D-glucosidase, $\beta$-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the CR3 modulator may be radiolabeled and combined, for example, with PMN, after which binding studies would be carried out using for example, C3bi-coated erythrocytes. Solutions would then be prepared that contain various quantities of labeled and unlabeled CR3 modulator and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

In a further embodiment of this invention, commercial test kits suitable for use by a medical specialist may be prepared to determine the presence or absence of CR3 modulator in a suspected mammalian host. In accordance with the testing techniques discussed above, one class of such kits will contain at least the labeled CR3 modulator or its binding partner, for instance an antagonist specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the reaction of a mammalian host to invasive stimuli, comprising:
(a) a predetermined amount of at least one labeled immunochemically reactive component obtained by the direct or indirect attachment of the present CR3 modulator or a specific binding partner thereto, to a detectable label;
(b) other reagents; and
(c) directions for use of said kit.

More specifically, the diagnostic test kit may comprise:
(a) a known amount of the CR3 modulator as described above (or a binding partner) generally bound to a solid phase to form an immunosorbent, or in the alternative, bound to a suitable tag, or plural such end products, etc. (or their binding partners) one of each;
(b) if necessary, other reagents; and
(c) directions for use of said test kit.

In a further variation, the test kit may be prepared and used for the purposes stated above, which operates according to a predetermined protocol (e.g. "competitive", "sandwich", "double antibody", etc.), and comprises:
(a) a labeled component which has been obtained by coupling the CR3 modulator to a detectable label;
(b) one or more additional immunochemical reagents of which at least one reagent is a ligand or an immobilized ligand, which ligand is selected from the group consisting of:
(i) a ligand capable of binding with the labeled component (a);
(ii) a ligand capable of binding with a binding partner of the labeled component (a);
(iii) a ligand capable of binding with at least one of the component(s) to be determined; and
(iv) a ligand capable of binding with at least one of the binding partners of at least one of the component(s) to be determined; and
(c) directions for the performance of a protocol for the detection and/or determination of one or more components of an immunochemical reaction between the CR3 modulator and a specific binding partner thereto.

In accordance with the above, an assay system for screening potential drugs effective to modulate the activity of the CR3 modulator may be prepared. The CR3 modulator is incubated with neutrophils in the presence of the prospective drug and then may be introduced into a cellular test system such as C3bi-coated erythrocytes, and the culture thereafter examined to observe any changes in the binding activity of the neutrophils.

An alternative drug screening assay contemplates the incubation of neutrophils with the CR3 modulator in the absence of the prospective drug, followed by introduction of the incubated neutrophils and the drug under test to the cellular test system to observe resultant binding activity.

A variant drug assay could be conducted by culturing a sample of test cells such as PMN which has the receptor CD18, or a sample of purified surface, in a medium containing the C3bi-coated erythrocytes. The drug under test could be added to the resulting culture and the reactivity of the CR3 modulator with the receptor on the test cells could thereafter be measured as a function of binding of EC3bi to CD18 to determine whether the prospective drug possessed any activity in the inhibition of the activity of the CR3 modulator.

An additional method for detecting antagonists of CR3 modulator activity may employ incubation of cells bearing CD18 or purified, surface-bound CD18 with labelled CR3 modulator in the presence of the prospective drug. Effectiveness of the drug in blocking interaction of the CR3 modulator with CD18 is measured by blockade of the binding of the labelled CR3 modulator to the cells or the surface-bound CD18.

An assay system for screening drugs which block or antagonize CR3 modulator synthesis promoters may also be prepared. In this assay, PMN are incubated with the prospective drug and an agonist of PMN, such as PMA, PAF, TNF, fNLLP, IL-8 and the like. To measure the effectiveness of the drug, the CR3 modulator content of the preparation may be measured by the above methods. Alternatively, the effectiveness of the drug may be ascertained by measurement of the binding of EC3bi to the PMN.

An assay for drugs that block or antagonize CR3 modulator synthesis promoters could also be conducted by measuring the ability of a test drug to prevent the accumulation of the precursors of CR3 modulator in cells treated with the drug and stimulated with an agonist.

An assay for drugs that block or antagonize CR3 modulator synthesis promoters could also be conducted by measuring the conversion of precursors of the CR3 modulator into the CR3 modulator. Appropriately labelled precursors of the CR3 modulator are added to activated PMN or to extracts of activated cells in the presence of the prospective drug. The presence of label in the CR3 modulator is then measured by the above assays, or by measuring the migration of label in appropriate chromatographic systems. This assay system is particularly useful for discovering drugs that block the actions of the enzymes that synthesize the CR3 modulator and is a particularly useful embodiment of the present invention.

The following examples set forth the details of the isolation and identification of the present CR3 modulator, and observations noted as to its activity, defining both the distinctions and similarities in activity between the present CR3 modulator and those factors identified earlier both by applicant and by others in the field. Naturally, the specific materials and techniques set forth hereinafter are exemplary only and may vary, so that the following is presented as illustrative but not restrictive of the present invention.

EXAMPLE 1

Isolation of CMF-1

A pellet of resting or stimulated PMN was stirred in chloroform:methanol:water = 10:10:1, with at least 3 solvent changes, for a minimum of 36 hours (see FIG. 1). Supernatants were dried down under vacuum and resuspended in chloroform:methanol:water=30:60:8. The solution of extracted lipids was applied to a DEAE-sephadex column, the column was washed with 6 bed volumes of solvent, and the anionic lipids eluted with the same solvent containing 0.065 M sodium acetate. The eluate was dried down under vacuum and resuspended in distilled water. Salt was removed by passage over a $C_{18}$ Sep-Pak reverse phase cartridge, followed by extensive washing with water. The lipids were eluted from the cartridge with chloroform:methanol = 1:1, dried down and stored in chloroform:methanol = 2:1. This material was used for the succeeding functional studies unless otherwise noted. This partially purified solution of CMF-1 contained many other acidic lipids, primarily gangliosides, as determined by thin layer chromatography (data not shown). Further purification may be accomplished by a Folch partitioning step. Briefly, lipid extract was dried down and resuspended in a two phase system of chloroform/methanol=2/1 and saline. The aqueous phase contained the CMF-1 activity while any remaining non-acidic contaminants localized to the organic phase and were removed. In quantitating the purification we found that less than 0.1% of CMF-1 activity is found in the flow-through from the DEAE and Sep-Pak columns. However, up to 50% of CMF-1 activity is lost in the Folch cut. Since the activity is not recovered in the organic phase, we presume the procedure destroys CMF-1 activity and therefore it is usually omitted from isolations of CMF-1.

The next step of purification employs a semi-preparative Versa-Pak $C_{18}$ reverse phase column eluted with a gradient of water to acetonitrile at 1% per minute. CMF-1 elutes at 50–55% acetonitrile on this column (see FIG. 2). The fine discrimination achievable by reverse phase chromatography, coupled with the purity of material as determined by ultraviolet spectroscopy (see FIG. 14 below) and by size exclusion chromatography (see FIG. 16 below), suggest that this purification procedure isolates CMF-1 as a single entity.

EXAMPLE 2

Biological Properties of CMF-1

Figure 3:
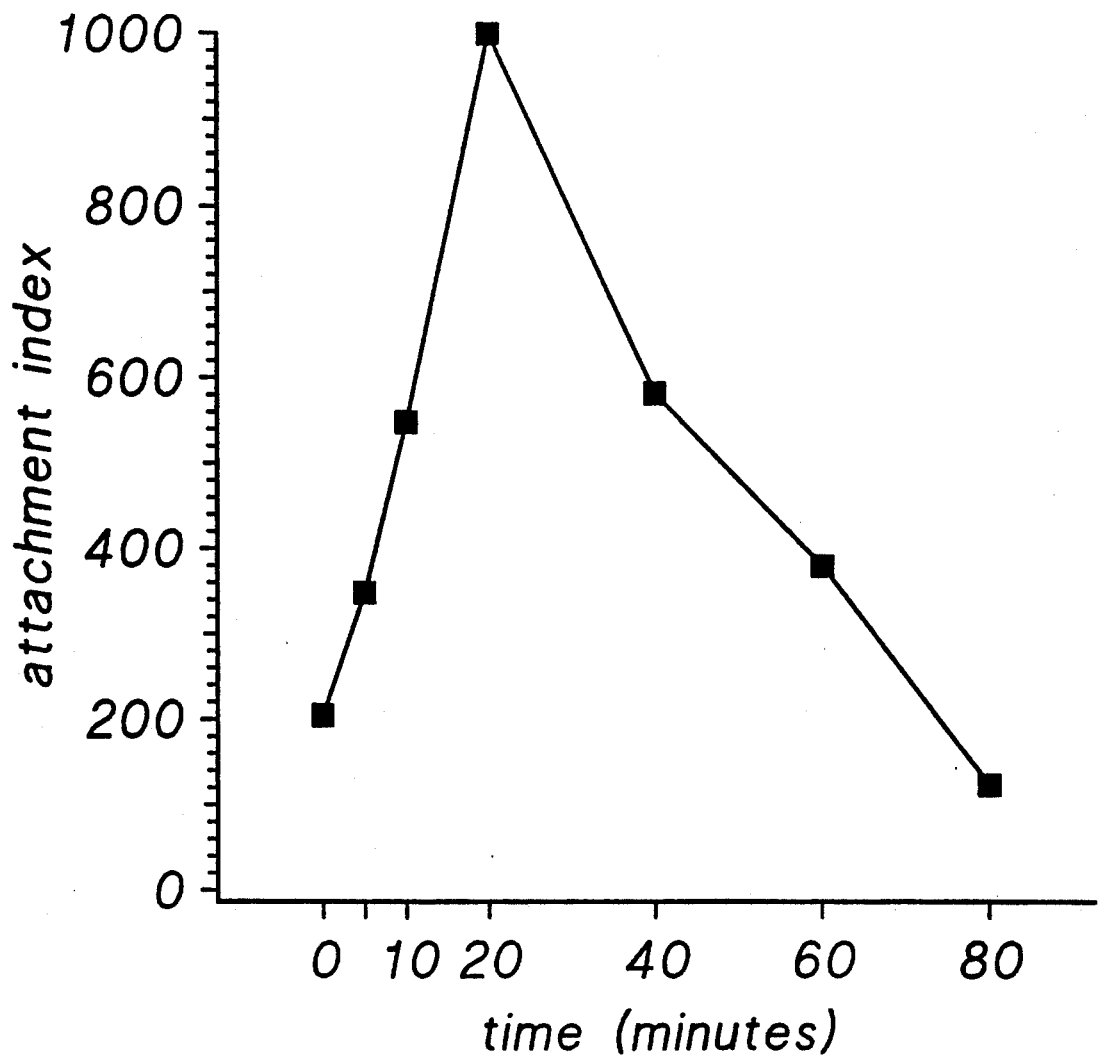
FIG. 3 is a graph showing the time course of EC3bi binding by PMN after treatment with CMF-1. Partially purified CMF-1 (42 units/ml) was added to PMN for varying times in the rosetting assay. This experiment was representative of three repeats.

A. Lipids Extracted from Activated Cells Modulate the Binding Activity of Resting PMN CMF-1 was first recognized as a substance extracted from PMA-stimulated PMN that can increase the binding activity of CR3 on resting PMN. CMF-1 activity is detected by incubating freshly isolated PMN with CMF-1-containing extract for 15 minutes and then measuring the ability of the PMN to bind erythrocytes coated with C3bi (EC3bi). A unit of activity is defined as the amount of CMF-1 needed to half-maximally activate $1.2 \times 10^5$ PMN in the rosetting assay. $10^7$ PMN yield 3–10 units of activity in a typical CMF-1 extraction. This means that extract from 8–25 PMN can half-maximally activate a single cell in a volume of one nanoliter. CMF-1 can increase the attachment index 2- to 10-fold above background levels (see FIG. 3). In contrast, extracted lipids from resting PMN have no CMF-1 activity. Gangliosides which might copurify with CMF-1, such as GM2, GD1a and GT1b, had no effect on binding.

B. Rosetting Induced by CMF-1 is Inhibitable by Antibodies Against CR3 and C3bi CMF-1 increases rosetting via a specific effect on binding of CR3 to C3bi (Table 1), since the increase in binding observed after addition of CMF-1 can be blocked by antibodies against either C3bi (mAb C39), CR3 α chain (mAb OKM10), or CR3 β chain (mAb IB4). Irrelevant antibodies such as OKMI, a non-blocking antibody against the α chain of CR3, had no effect on EC3bi rosetting.

C. CMF-1 Transiently Increases Binding Activity of CR3

Figure 4:
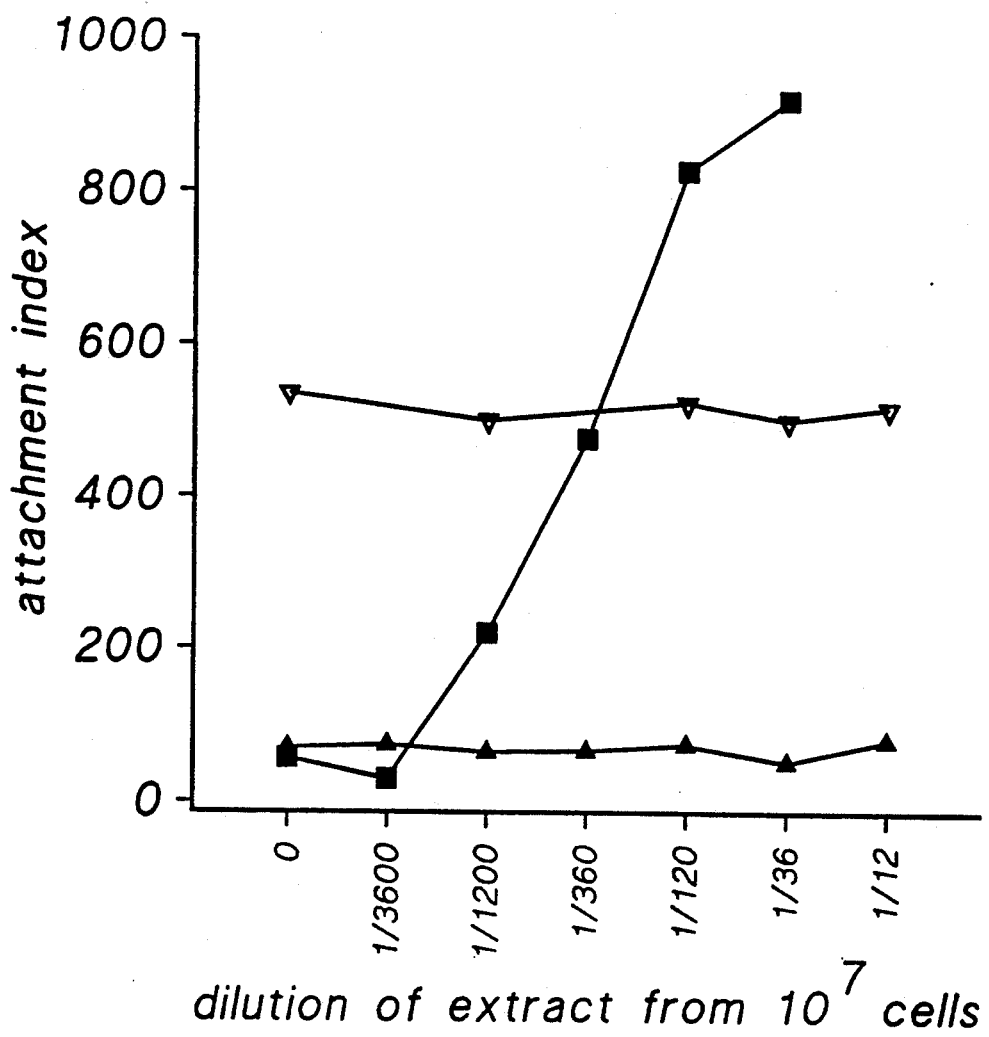
FIG. 4 is a graph illustrating the dose response of EC3bi binding by PMN treated with CMF-1. Partially purified lipids extracted from PMA-stimulated cells were diluted and applied to PMN for 15 minutes in the rosetting assay (solid squares). Half-maximal binding occurred at a 1/360 dilution, which means 6 units of CMF-1 were extracted from $10^7$ cells in this preparation. Lipids extracted from resting PMN (solid triangles) had no CMF-1 activity at any dilution. CMF-1 had no effect on binding of PMN to erythrocytes coated with IgG (EIgG, open triangles).

CMF-1 added to resting PMN in a rosetting assay induces CR3 binding to EC3bi with a time course similar to agonists such as PMA (Table 2). CMF-1 increases rosetting to maximal levels by 20 minutes. Rosetting then returns to baseline levels by 60–80 minutes. Lipid extracts from resting PMN have no effect for any length of time (attachment index <55). Neither CMF-1 nor lipids from resting cells have any effect on the binding activity of a distinct receptor on PMN, Fc RIII, as measured by rosetting of E coated with IgG particles (EIgG, see FIG. 4, open triangles).

D. The Effect of CMF-1 is Dose-Dependent

The effect of CMF-1 (FIG. 4, solid squares) on CR3 binding is dose-dependent. Lipids from untreated PMN (solid triangles) have no effect on CR3 binding activity, even when barely diluted (1/12). EIgG rosetting (open triangles) was unaffected by CMF-1. For this CMF-1 preparation, one unit corresponds to 1/360 dilution of extract. This means $10^7$ cells yielded 3 units.

E. CMF-1 Production Correlates with CR3 Binding Activity

Since CMF-1 can activate the binding activity of CR3, we postulated that changes in CMF-1 levels normally control CR3 activity. We tested this hypothesis by measuring the amount of CMF-1 that can be obtained from resting or stimulated cells. Resting cells have very low CR3 activity and no CMF-1 could be extracted (Table 3). After 20 minutes of stimulation with PMA, CR3 activity is maximal and a great deal of CMF-1 could be obtained from the cells. Further incubation with PMA for a total of 60 minutes leads to a reduction of CR3 activity to baseline, and no CMF could be extracted from the cells.

All PMN agonists tested so far trigger CMF-1 production by PMN at time points coinciding with peak CR3 binding activity. No agonist that increases CR3 activity in PMN has yet been found that fails to trigger CMF-1 production. Thus, CMF-1 content is closely correlated with the activity of CR3.

F. CMF-1 is not equivalent to PMA or PAF

The data thus far are consistent with the possibility that the PMA used to activate the extracted PMN, which is a lipid, may be a contaminant in the partially purified lipid extract and is responsible for CMF-1 activity. Several pieces of evidence indicate that this is not the case. Extracts from cells treated with $^3$H-PMA contained too few counts coeluting with the CMF-1 activity for the activity to be due to PMA. PMA is sensitive to hydrolysis in water and the extract is in aqueous solution for a minimum of 12 hours during the purification. Finally, and most convincingly, treatment of PMN with a variety of different agonists which activate CR3, both lipids and proteins, all result in CMF-1 production. CMF-1 is produced by PMN stimulated with tumor necrosis factor (TNF, $5 \times 10^3$ u/ml, 15'), platelet activating factor (PAF, 100 nM, 15') and formylnorLeu-Leu-Phe (fNLLP, $5 \times 10^{-8}$M, 5-15') as well as by PMN stimulated with PMA (30 ng/ml, 20'). The native conformation of proteins can be completely disrupted by exposure to organic solvents. Tumor necrosis factor, for example, would be unable to maintain its active configuration after extraction in chloroform/methanol, and so is unlikely to be a contaminant responsible for the CR3 modulating activity in the extract.

Platelet activating factor (PAF), or L-α-phosphatidylcholine, β-acetyl- -O-alkyl, is a lipid produced by PMN in response to agonists (reviewed in M. Baggiolini et al., 1988), that can increase CR3 binding activity. PAF is thus another potential contaminant in the lipid extract that may account for CMF-1 activity. To rule out that CMF-1 is equivalent to PAF, an antagonist, WEB 2086, was added at concentrations that completely block 100 nM PAF-induced rosetting of EC3bi. The antagonist had no effect on CMF-1-induced rosetting (Table 4).

G. CMF-1 Does Not Induce TNF Production by Whole Blood

Figure 5:
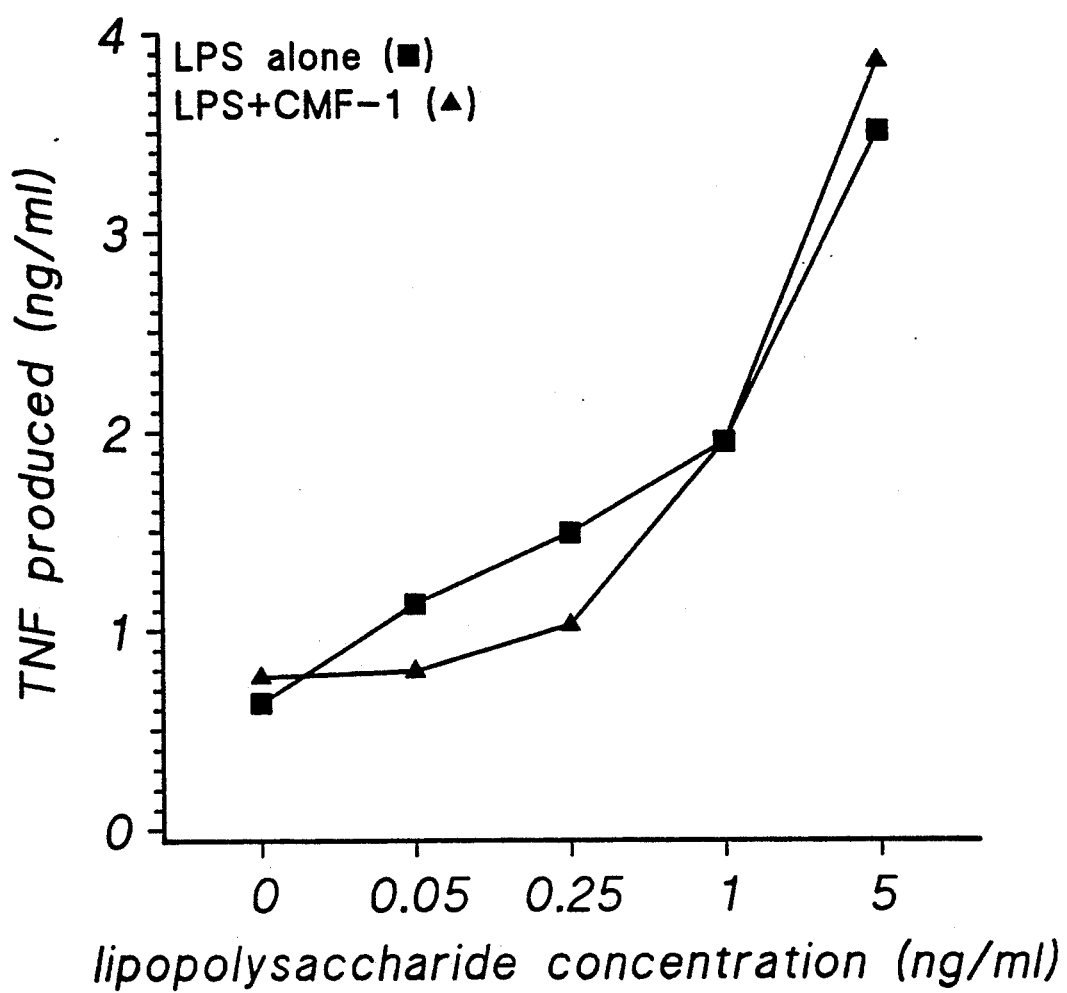
FIG. 5 is a graph illustrating that CMF-1 does not trigger TNF production by cells in whole blood. Whole blood was incubated for 5 hours at 37° C. with lipopolysaccharide (LPS), CMF-1 (42 units/ml) or both. After spinning out the cells, supernatants were tested for the presence of tumor necrosis factor (TNF) by radioimmunoassay. This experiment was representative of two repeats.

Unlike LPS, CMF-1 (42 units/ml) does not cause TNF production in whole blood, suggesting CMF-1 activity is not due to contamination with LPS (FIG. 5). Whole blood was incubated 5 hours at 37.C with LPS, CMF-1 or both. Cells were spun out and the supernatant was tested for secreted TNF by radioimmunoassay. Each data point corresponds to the average of six wells. These data indicate that CMF does not initiate TNF secretion and confirmed that CMF-1 is not contaminated with LPS.

H. CMF-1 Increases Binding Activity of CR3 at the LPS Binding Site

CR3 binds to a variety of ligands besides C3bi and so we tested whether CMF-1 can effect binding of these ligands as well. We observed binding of lipopolysaccharide (LPS) by measuring attachment of erythrocytes which have lipid IVa incorporated into the surface leaflet of the plasma membrane (EIVa). Lipid IVa is a metabolic precursor of LPS and is recognized by CR3 (8). We found that CMF-1 causes coordinate increases in binding of C3bi and IVa (Table 5).

I. CMF-1 Increases Binding Activity of CR3 for Fibrinogen and Endothelial Cells The binding of CR3 to fibrinogen can be measured by studying the attachment of PMN to fibrinogen-coated surfaces. CMF-1 enhances PMN binding to a plastic surface coated with fibrinogen (Table 6). The binding is CD18 dependent, since it can be blocked by antibodies against the β chain of CR3 but not by an irrelevant antibody against MHC class I. Values shown are the average of duplicate wells.

Figure 6:
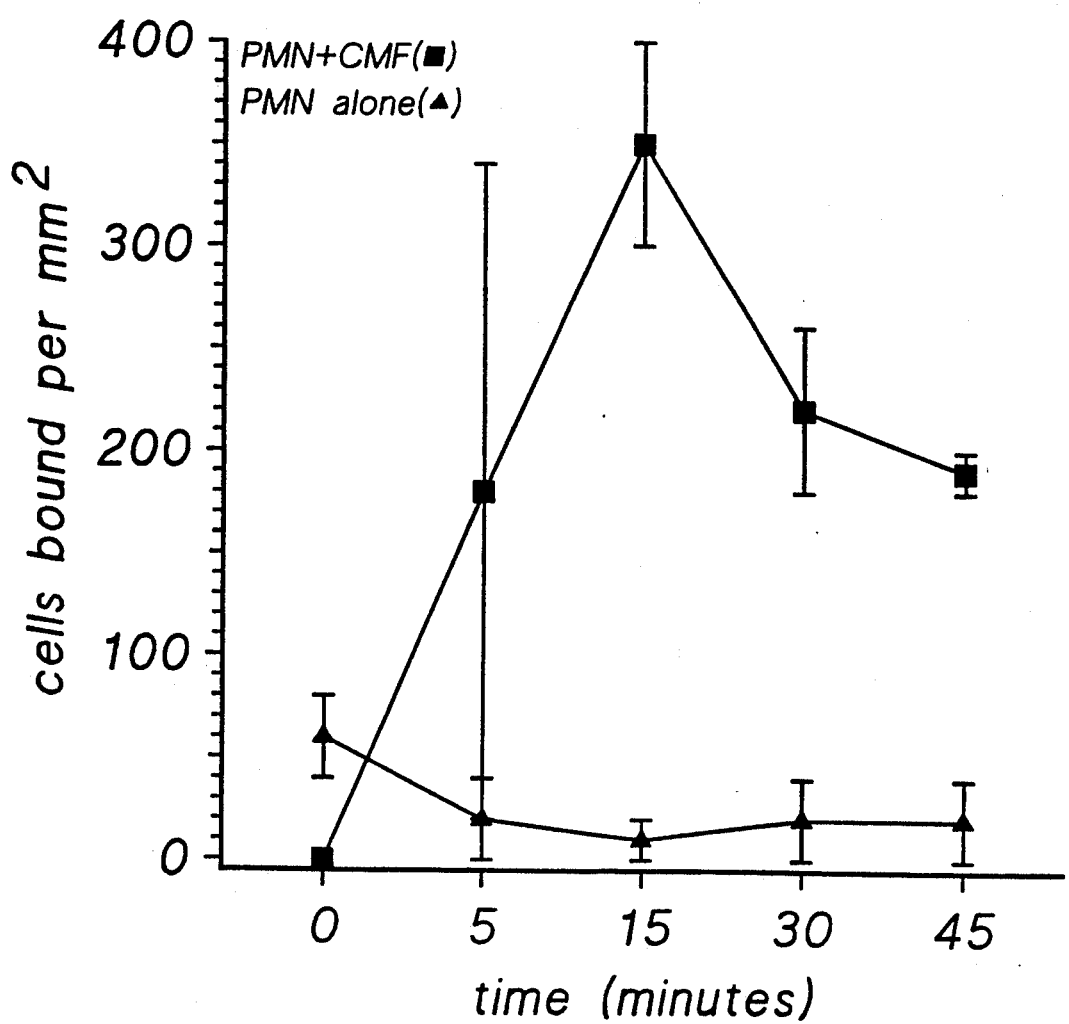
FIG. 6 is a graph depicting the time course of CMF-1-induced binding of PMN to fibrinogen-coated surfaces. PMN was allowed to adhere to fibrinogen-coated surfaces at 37° C. for varying times in the presence (squares) or absence (triangles) of 42 u/ml of CMF-1, partially purified from fNLLP treated cells. Data points are the average of two experiments, two wells each.

The time course of fibrinogen binding by PMN in response to CMF-1 (42 units/ml) is similar to that in response to PMA (FIG. 6). Binding increases to 15 minutes, and then declines. Untreated PMN bind poorly to fibrinogen. Lipids extracted from resting PMN (1/36 dilution of extract from $10^7$ cells) did not increase binding to fibrinogen (46 cells ±20 bound per mm$^2$). Values shown are the average of two experiments, duplicate wells in each.

Figure 7:
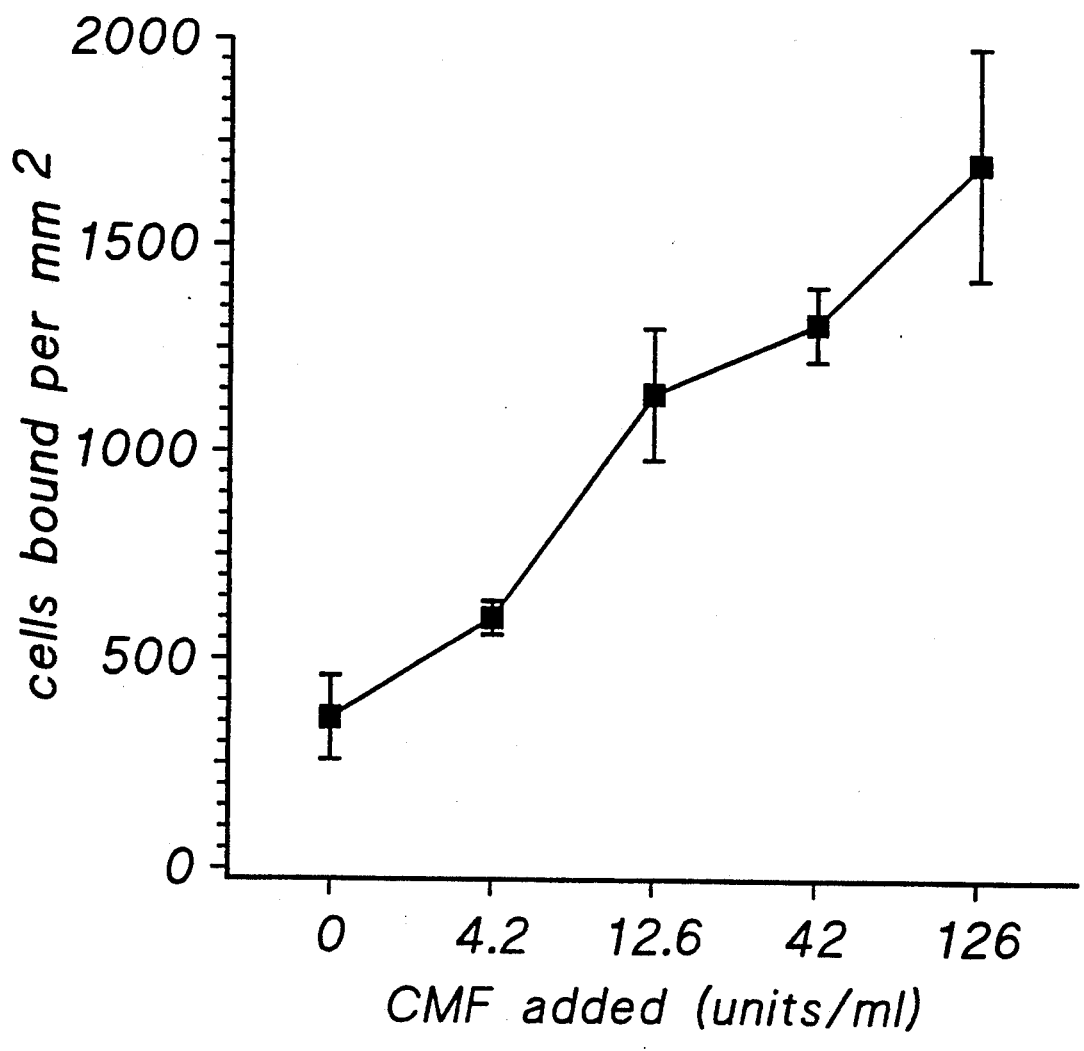
FIG. 7 is a graph illustrating the dose response of binding of CMF-1 treated PMN to unstimulated endothelium. PMN were stimulated for 15 minutes, 37° C. with varying amounts of CMF-1, washed free of agonist and applied to unstimulated human umbilical vein endothelial cell monolayers (EC). Binding to EC was allowed to occur for 15 minutes, 37° C. before washing and counting bound cells by phase-contrast microscopy. Numbers are the average of two experiments, two wells each.
Figure 8:
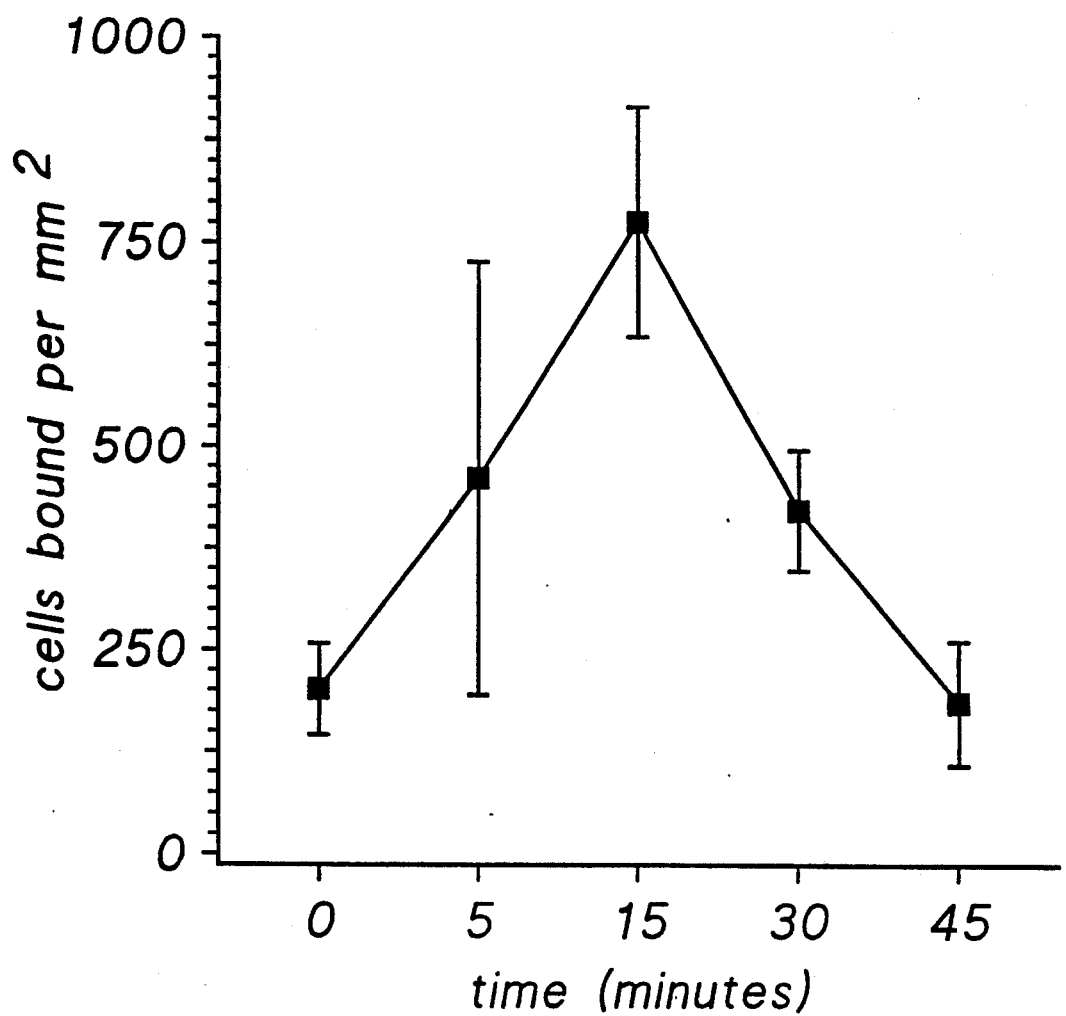
FIG. 8 is a graph depicting the time course of binding of CMF-1 treated PMN to unstimulated endothelium. PMN were stimulated for varying times with CMF-1 (42 u/ml, partially purified from fNLLP treated cells) and tested for EC binding as described in FIG. 7. Data is the average of two experiments, two wells each.
Figure 9:
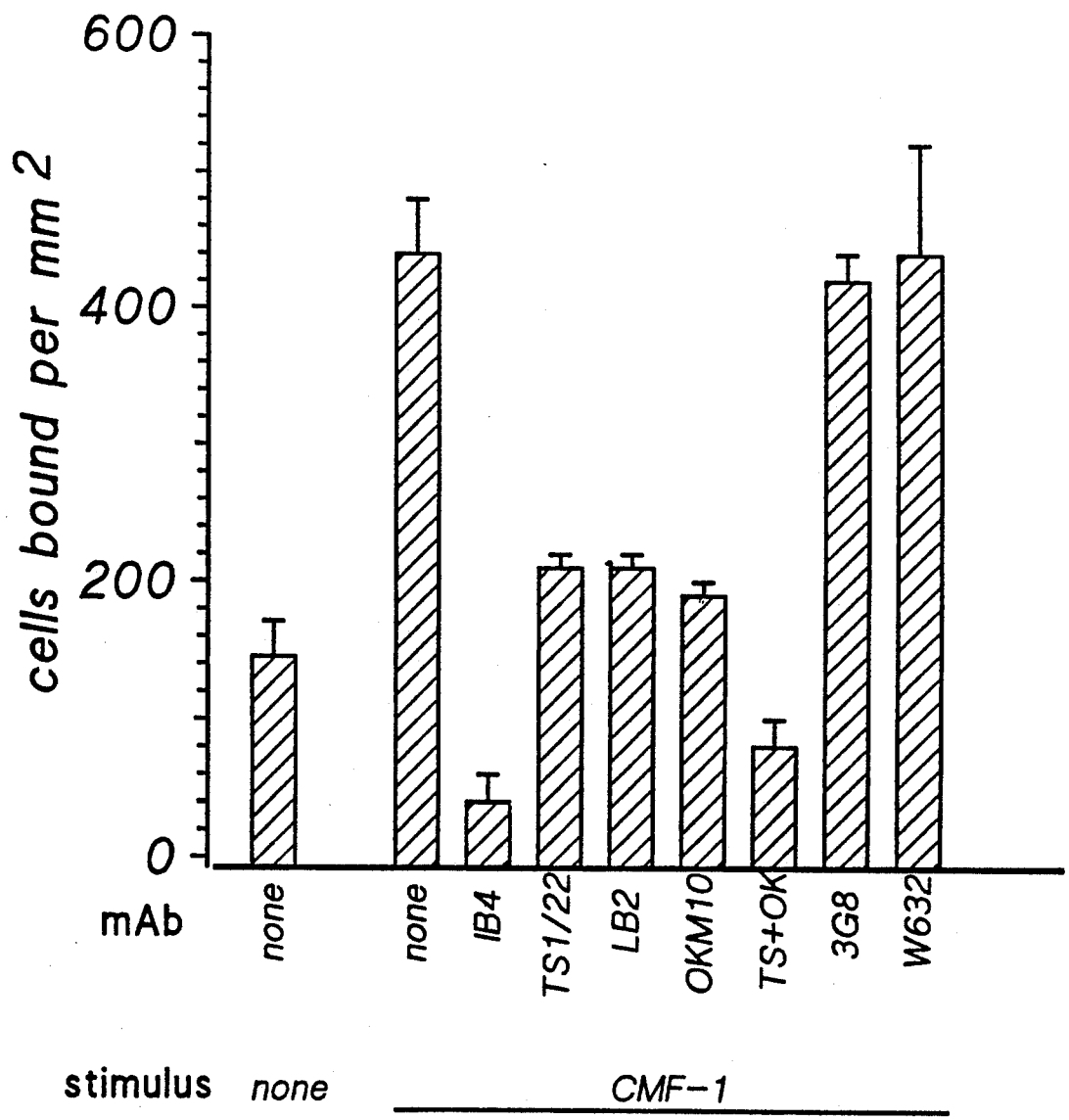
FIG. 9 is a graph illustrating the binding of CMF-1 treated PMN to unstimulated endothelium is due to CR3 and LFA-1. PMN were tested for EC binding as described, in the presence or absence of mAbs (10 μg/ml). Values are the average of duplicate wells. This experiment was representative of three repeats.

PMN bind unstimulated endothelial cells (EC) via CR3 and LFA-1 (S. K. Lo et al., 1989). The ligand for CR3 on endothelial cells has not yet been characterized, while the same β chain as CR3, binds to ICAM-1 on the EC. The binding interaction between stimulated PMN and unstimulated EC also occurs in a regulated manner, increasing transiently after PMN are treated with phorbol esters, peaking at 20 minutes, and returning to baseline by 60 minutes (S. K. Lo et al., 1989). We treated PMN with CMF-1 then added them to an unstimulated EC monolayer. CMF-1 augmented binding of PMN to EC in a dose dependent manner (FIG. 7). Binding levels peaked at 15 minutes and declined to baseline by 45 minutes (FIG. 8). Finally, the ability of antibodies to block this binding was identical to that seen when cells were treated with phorbol esters (FIG. 9). Antibody to the common β chain of CR3 and LFA-1 (IB4) blocks completely while antibodies to the LFA-1 α chain (TS/122) or CR3 α chain (OKM10), or to ICAM-1 (LB2), block binding by approximately 50%. The two anti-α chain antibodies, when added together, are able to block binding entirely while antibodies to MHC class I (W632) or Fc RIII (3G8) on PMN do not affect binding to EC at all. These results suggest that LFA-1, another integrin closely related to CR3, may be regulated by CMF-1. They also indicate that CMF-1 controls the interaction of PMN with endothelium.

Figure 10:
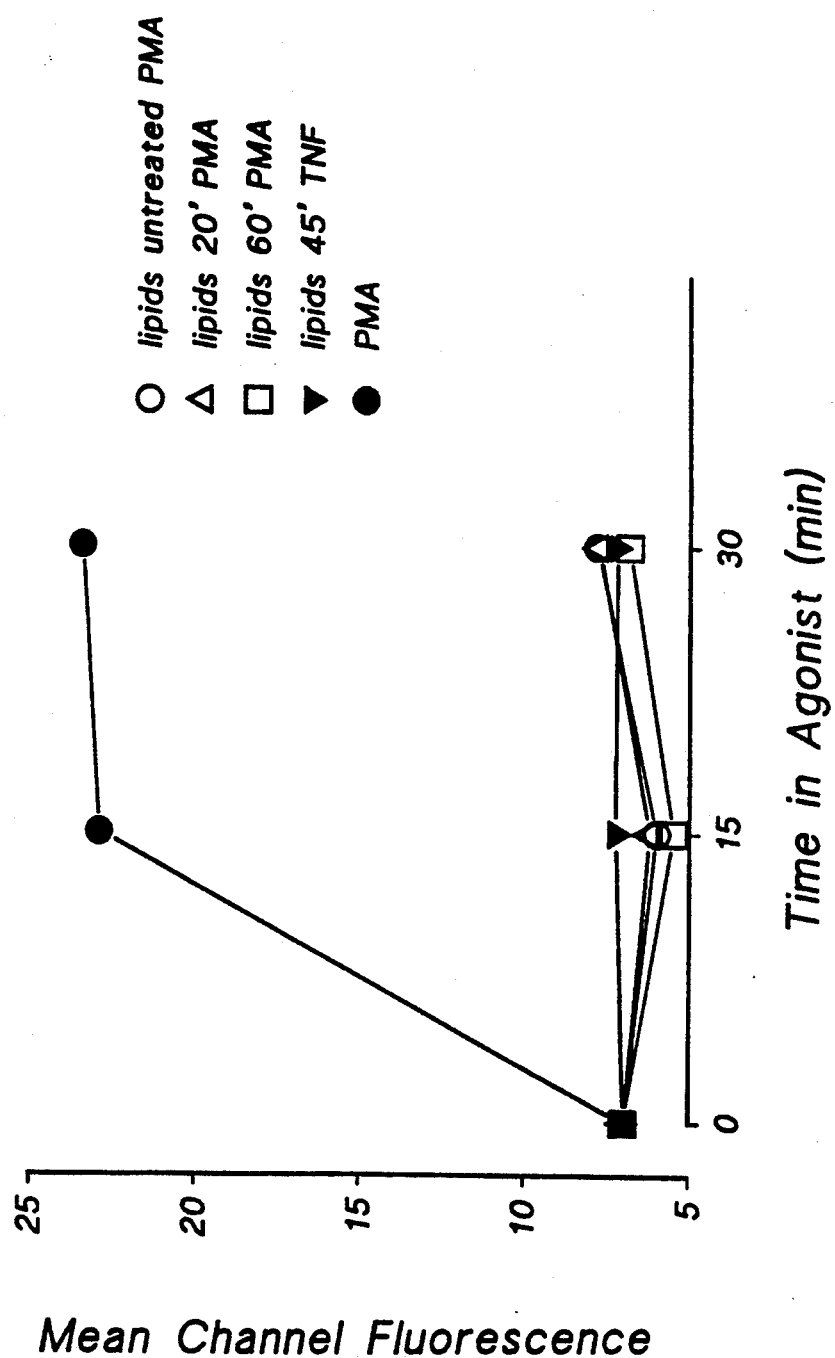
FIG. 10 is a graph demonstrating that CMF-1 does not cause PMN degranulation. PMN were incubated with lipid extracts or PMA for varying times, washed and stained with a mAB against CD11b (OKM10, 5 μg/ml) and a fluorescein-conjugated secondary antibody. Cells were then analyzed by flow cytometry. PMA was used at 30 ng/ml. The lipid extracts used in this experiment derived from PMN treated for varying times with different agonists. Lipids from cells treated with PMA for 20 minutes had 17 u/ml of CMF-1 activity, while those from cells treated with TNF for 45 minutes had 42 u/ml. Lipids from cells treated 0 or 60 minutes with PMA had <2 u/ml and 4 u/ml CMF-1 activity respectively (see Table 3). This experiment was representative of three repeats.

J. CMF-1 is Unlike Traditional PMN Agonists in that it Does Not Cause Degranulation It is possible that CMF-1 acts as an agonist itself by triggering a cascade of events throughout the cell. Alternatively, it could act exclusively at the level of CR3, perhaps binding to the receptor itself and modifying its binding affinity for ligand. To address these possibilities, we asked whether CMF-1 acts like an agonist in triggering cellular responses unrelated to CR3. One common response of PMN to agonists is release of specific granules. Addition of a lipid extract from PMA or TNF treated PMN, which contained CMF-1 activity by rosetting assay, did not change the level of CR3 expression, a measure of the release of CR3 from intracellular pools upon degranulation (FIG. 10). By contrast, PMA itself increased CR3 expression by about 3-fold after 15 minutes. As a control, lipids extracted from cells which do not have CMF-1 activity (i.e., resting PMN or PMN treated with PMA for 60 minutes), also did not change CR3 expression.

CR3 Activated with PMA can be Restimulated with CMF-1

Figure 11:
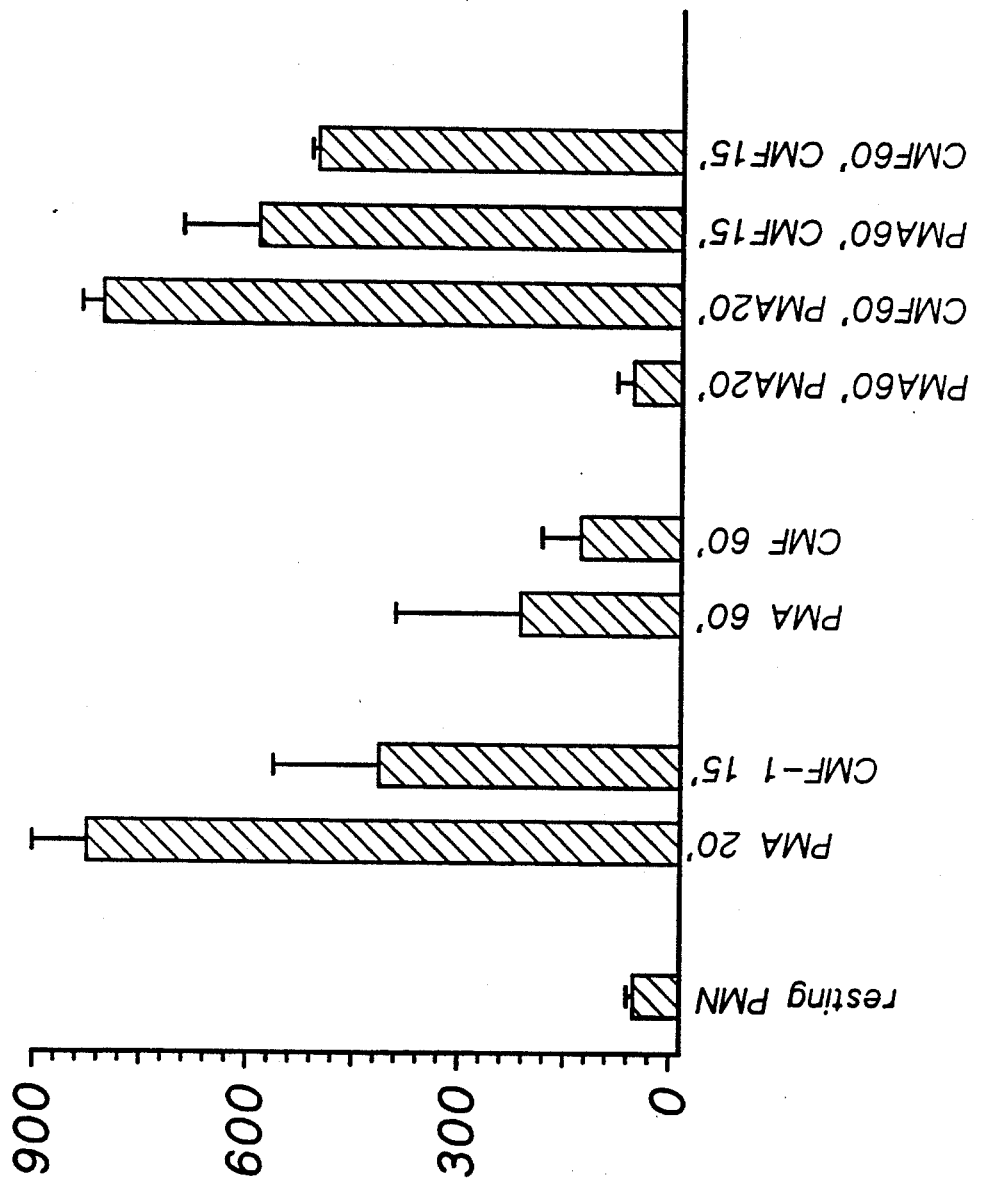
FIG. 11 is a graph demonstrating that cells stimulated with PMA can be restimulated with CMF-1. Cells were stimulated with PMA (30 ng/ml) or CMF-1 (42 u/ml, partially purified from fNLLP treated cells) for indicated times, washed, and then stimulated with another agonist where indicated. Agonists were washed away before applying EC3bi and measuring rosetting in the usual way. These data are the average of two experiments, three wells in each.

PMA activates protein kinase C in PMN and exhausts the intracellular signalling system such that the cell becomes refractory to restimulation with PMA after 60 minutes (AHV and SDW, unpublished results). We asked whether CMF-1 can restimulate cells treated with PMA. If CMF-1 acts at the level of the receptor, then exogenous CMF-1 should work as well in a cell that can no longer respond to upstream signals. Indeed, a cell treated with PMA (30 ng/ml) for 60 minutes, followed by CMF-1 (42 u/ml) for 15 minutes, and then tested for rosetting to EC3bi, responds equally well if not better than a cell exposed to CMF-1 alone (FIG. 11). Cells treated with CMF-1 can be restimulated with CMF-1 as well.

L. CMF-1.Activity can be Immunoprecipitated with CD18

The mode of action of CMF-1 suggests a direct association between it and the CR3 receptor. To test this hypothesis, PMN stimulated with PMA were lysed at the critical micellar concentration of the detergent octylglucoside so as to minimize disruption of native lipids surrounding CR3 on the cell surface, and the lysate was immunoprecipitated with sepharose bearing antibody to the $\beta$ chain (CD18) of CR3. The pellet was washed well and extracted with chloroform:methanol=2:1 to remove any lipids still associated with the receptor. This lipid extract was then tested in a rosetting assay for CMF-1 activity, and was in fact found to contain CMF-1 (table 7). Sepharose beads alone failed to coprecipitate an CMF-1 activity.

M. Activated PMN do not Secrete Significant Quantities of CMF-1

Figure 12:
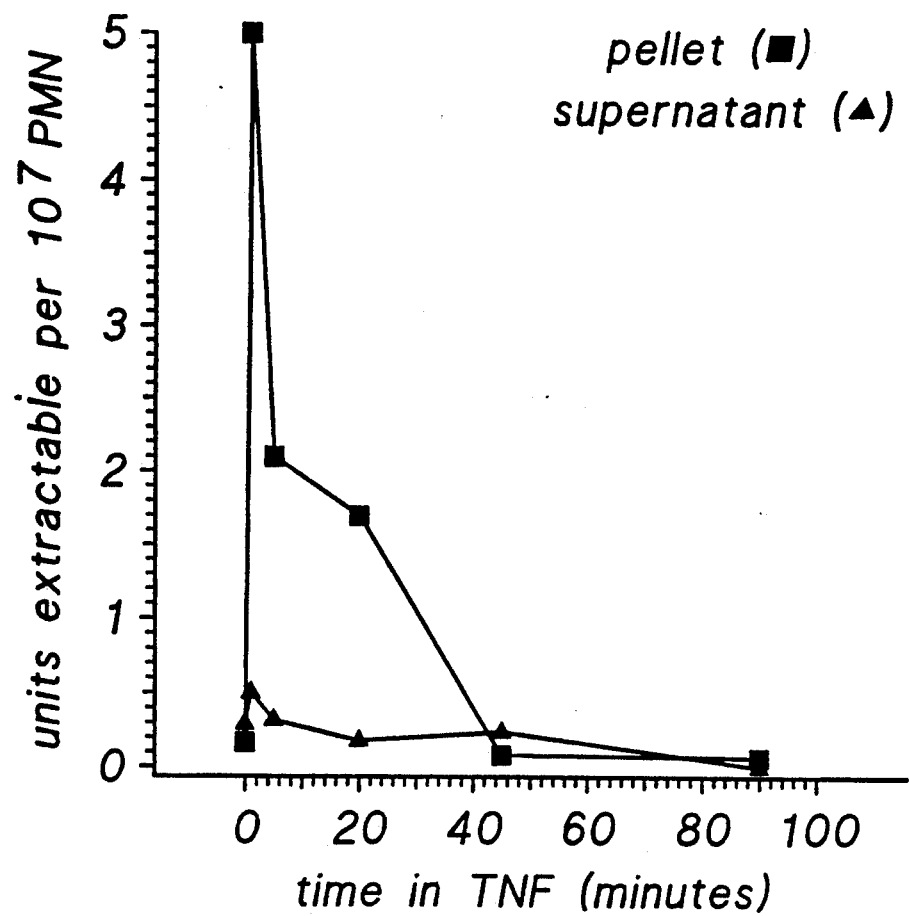
FIG. 12 is a graph demonstrating that the majority of CMF-1 produced by activated PMN is cell associated. PMN was exposed to TNF ($5 \times 10^3$ u/ml) for varying times and spun down. Pellets were extracted with chloroform: methanol:water=10:10:1 as described above, and supernatants were dried down in a rotary evaporator and resuspended into chloroform:methanol=2:1. The extracts were then tested for CMF-1 activity by rosetting assay.

CMF-1 can be extracted from pellets of stimulated PMN. To determine if CMF-1 is secreted by these cells, the medium of stimulated cells was dried down and extracted for lipids, and then tested for CMF-1 activity. As shown in FIG. 12, the number of units extractable from cell supernatants (squares) was always far less than that derived from the cells themselves (triangles). Therefore, PMN do not secrete significant quantities of CMF-1.

N. CMF-1 Increases Adhesion Mediated by LFA-1

Figure 13:
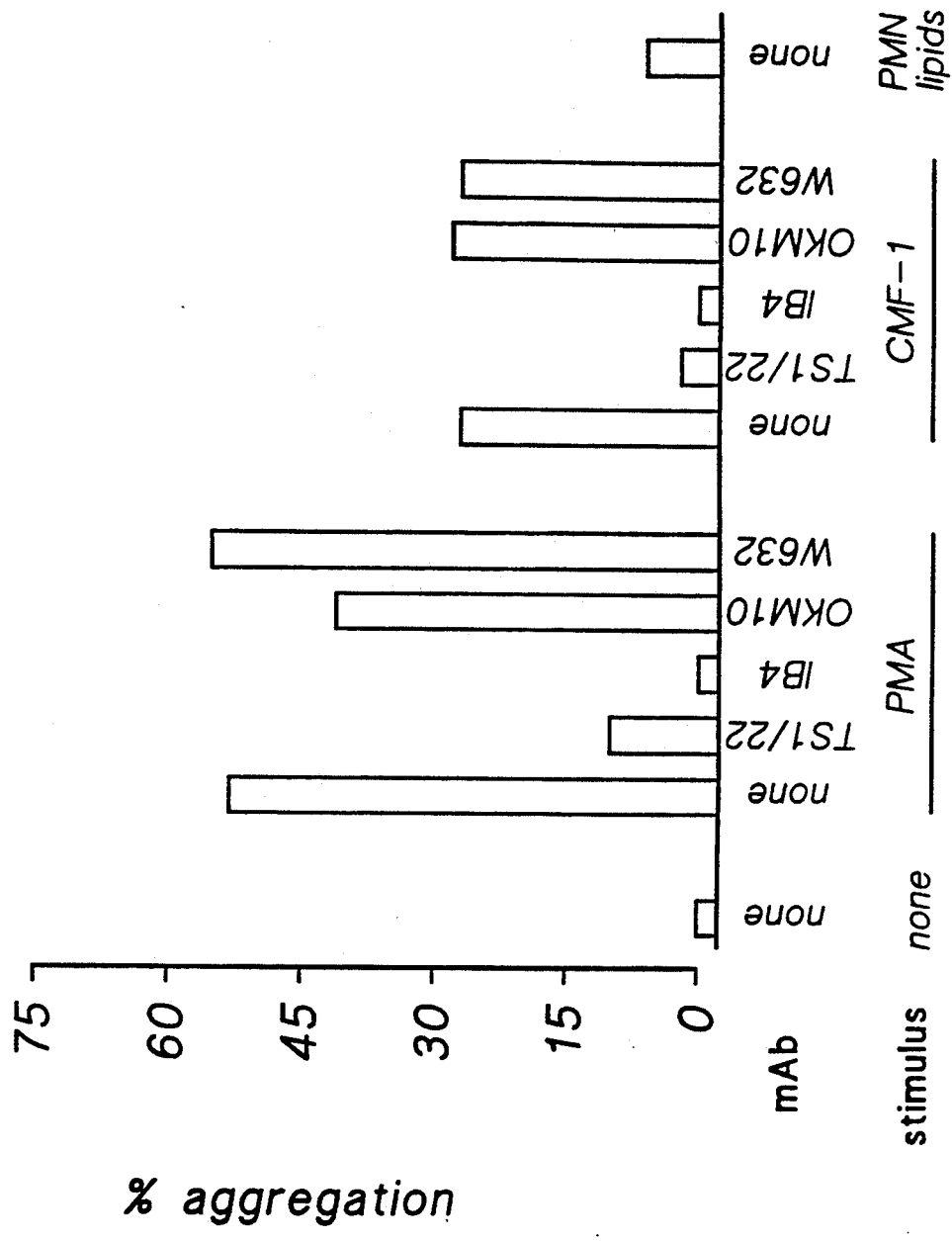
FIG. 13 is a graph demonstrating that CMF-1 stimulates lymphocyte aggregation via LFA-1. Lymphocytes were purified on Percoll gradients as described (16). Contaminating monocytes were removed by plastic adherence. Cells were then added to Terasaki plate wells and PMA (100 ng/ml), CMF-1 (42 u/ml) or lipids extracted from resting PMN ("PMN lipids", extracted from 3 times as many cells as the CMF-1) were added in the presence or absence of antibodies (10 μg/ml). TS1/22 and OKM10 are against CD11a and CD11b, respectively. IB4 is against CD18. W632 recognizes class I MHC. Lipids from resting PMN were diluted 1/30. Cells were incubated 30 minutes at 37° C. and aggregation was determined by phase-contrast microscopy according to the following formula: % aggregation=[1-(free cells per mm$^2$ in test well/free cells per mm$^2$ in control untreated wells)]×100. This experiment was representative of three repeats.

Since CMF-1 can increase binding between PMN and endothelial cells, and since this binding interaction is blocked by antibodies against LFA-1 as well as CR3, we tested the effect of CMF-1 on another regulated adhesion system that is known to be completely LFA-1 dependent. Human peripheral blood lymphocytes aggregate in response to PMA and can be prevented from doing so by antibodies to LFA-1 (M. Patarroyo et al., 1983; R. Rothlein et al., 1986). When CMF-1 was added to lymphocytes freshly isolated from whole blood, it caused homotypic aggregation to an extent comparable with that stimulated by PMA (FIG. 13), and the effect of either agonist was blocked by anti-LFA-1 $\beta$ chain and $\alpha$ chain but not by antibody against CR3 $\alpha$ chain or MHC class I. Also, lipids from unstimulated PMN, which lack CMF-1 activity, have no effect on lymphocytes.

EXAMPLE 3

Physical Characterization of CMF-1

A. Ultraviolet and Visible Spectroscopy

An ultraviolet and visible spectrum of pure CMF-1 is shown in FIG. 14, at left. The solvent blank is shown at right. CMF-1 has a max at 196nm with a slight shoulder out to 300 nm. The spectrum was flat between 300 and 800 nm (data not shown). This result rules out the possibility that CMF-1 contains peptide bonds, which absorb at 214 nm, nucleic acids, which absorb at 260 nm, and conjugated double bond systems, which absorb at wavelengths over 300 nm.

B. No Known Lipids Have CMF-1 Activity

In an effort to identify CMF-1, many well characterized lipids were tested for CMF-1 activity in the rosetting assay. Table 8 lists those tested, none of which were able to enhance rosetting of PMN to EC3bi.

C. CMF-1 is resistant to a variety of chemical modifications

Figure 15:
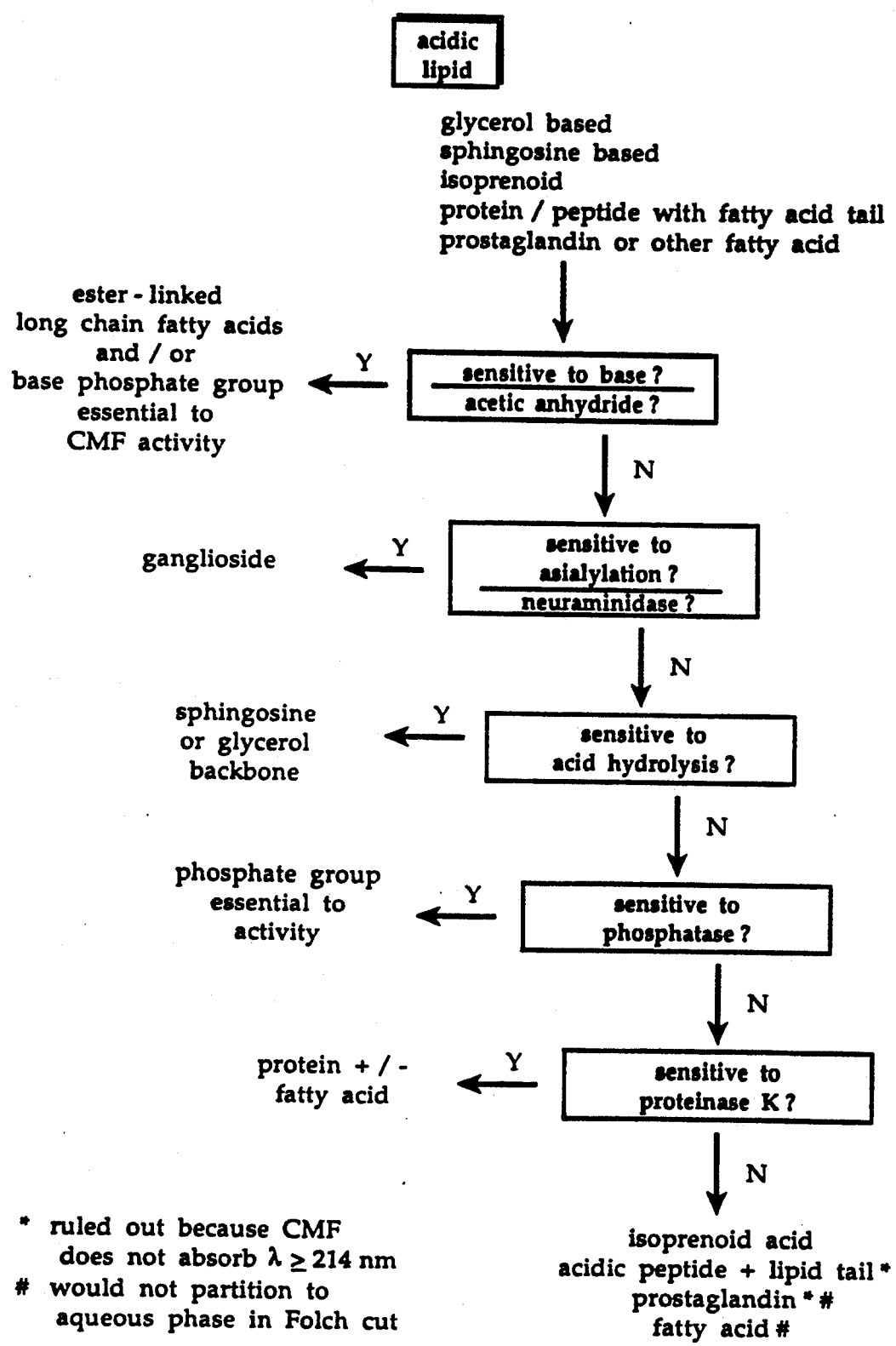
FIG. 15 is a flow chart summarizing experiments to clinically destroy CMF activity.

Classes of compounds with physical properties similar to those of CMF-1 include glycerol- or sphingosine-based lipids, eicosanoids, other fatty acids, isoprenoid lipids and proteins or peptides with a hydrophobic tail. All but isoprenoids were ruled out by subjecting CMF-1 to treatments that destroy particular classes. The details of the treatments are outlined in Table 9 and summarized below and in FIG. 15.

CMF-1 retained activity when treated with base (30% ammonium hydroxide or 1N NaOH) or acetic anhydride, suggesting it does not contain ester-linked fatty acids or a phosphate base. CMF-1 was not affected by desialylation with acetic acid or by neuraminidase, suggesting CMF-1 activity does not reside in a ganglioside. Acid hydrolysis (2N or 0.5N methanolic HCl) did not destroy activity, so CMF-1 does not have a sphingosine or glycerol backbone, or glycosidic bonds that are needed for activity. CMF-1 activity is unaffected by phosphatase or protease, suggesting that phosphate groups are not essential for activity and that CMF-1 does not have a protein structure.

In addition, reduction with sodium borohydride, oxidation with hydrogen peroxide, and periodate oxidation of vicinal hydroxyls all had no effect on CMF-1 activity. Of the original categories of candidate structures for CMF-1, the only ones that would remain unaffected by these treatments are isoprenoids and prostaglandins or fatty acids. A protease resistant peptide with a lipid tail is not a good possibility because CMF-1 does not absorb at 214 nm, the wavelength of absorption of the peptide bond. Prostaglandins and fatty acids are unlikely considering CMF-1 activity partitions to aqueous phase rather than the organic in a Folch partition, and since the former contain conjugated double bond systems, ruled out by the spectrograph. This leaves an isoprenoid structure as the most likely candidate for CMF-1.

One chemical treatment that was found to destroy CMF-1 activity is ozonolysis (Table 10). Ozone (2ppm) is generated by passage of a stream of oxygen over an ultraviolet light source and bubbled into a solution of CMF-1 in ethyl acetate for 15 minutes. This treatment adds oxygen across carbon-carbon double bonds and results in double bond cleavage, forming two aldehyde molecules. Isoprenoids have double bonds, so cleavage of CMF-1 by ozone is consistent with an isoprenoid structure.

D. CMF-1 has a Molecular Weight of Approximately 340 Daltons

Size exclusion chromatography was used to determine the molecular weight of CMF-1. A TSK G2000HXL size exclusion column with a separation range of zero to 2000 daltons was used. An isocratic run in tetrahydrofuran separated molecular weight standards to yield a calibration curve shown in FIG. 16 by the dark triangles. CMF-1, as measured by the rosette-inducing activity in each fraction, ran at 6.4 and 9.4 ml (histogram). Peaks of CMF-1 activity do not correspond to peaks of absorbance at 254 nm, as expected from the UV spectrum data. The 9.4 ml fraction corresponds to a molecular weight of 340 daltons $+/-16$. The 6.4 ml fraction is in the excluded volume of the column, suggesting that the CMF-1 running there has a molecular weight $>>2000$. Rerun of the material eluting at the excluded volume again yielded the two molecular weight species of CMF-1 activity. A rerun of the 340 MW fraction, after mixing with phosphatidylcholine, also yielded the two forms of CMF-1.

As a result of the above, it has been concluded that the two CMF-1 activities are in equilibrium with each other because they can interconvert and thus correspond to the same molecule running in either a monomeric (340) or micellar ($>>2000$) form.

E. CMF-1 is not equivalent to Leukotriene B4 or Lipoxin A4

Figure 17:
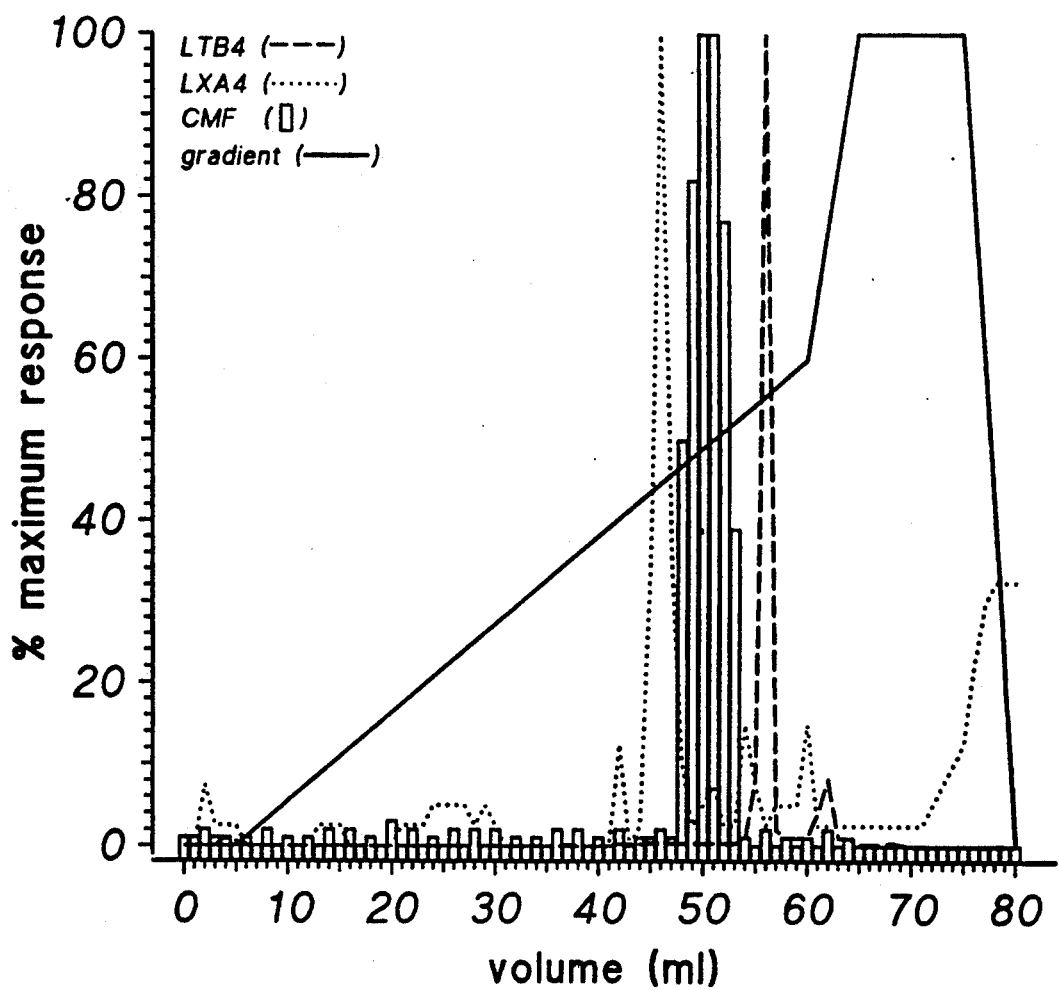
FIG. 17 is a graph demonstrating that CMF-1 is not equivalent to leukotriene B$_4$ or lipoxin A$_4$. A Waters μBondaPak C$_{18}$ a reverse phase column (10 μm particle size, 3.9 mm×150 mm) was loaded with CMF-1 (50 units, partially purified from fNLLP treated cells), LTB4 (5 ng, and 0.5μCi) or LXA4 (5 μg) and eluted with a 1% per minute gradient of water to acetonitrile (solid line). CMF-1 elution was monitored by rosetting assay (histogram), LTB4 by cpm per fraction (dashed line) and LXA4 by absorbance at 254 nm (dotted line).

The molecular weight of 340 daltons definitively rules out a ganglioside structure (MW>1000), as well as a glycerophosphatide (MW>500), but it is suggestive of an eicosanoid. To rule out two candidate eicosanoids with rosette-promoting capabilities (AHV and SDW, unpublished results), CMF-1 was run alongside $^3$H-leukotriene B4 (LTB4) and lipoxin A4 (LXA4) on a Waters µBondaPak C$_{18}$ reverse phase column (FIG. 17). The gradient was 1% per minute water to acetonitrile run from 0-60% acetonitrile (see solid line on graph for gradient profile). These conditions were known from previous runs on this column to elute CMF-1 at 45-50% acetonitrile. The LTB4 elution position was monitored by cpm present in each fraction (dashed line), LXA4 was monitored by absorbance at 254 nm (dotted line) and CMF-1 position was verified by assaying fractions for activity in the rosetting assay (histogram corresponds to attachment index). Neither eicosanoid coeluted with CMF-1. Moreover, concentrations of LTB4 or LXA4 capable of activating CR3 gave large peaks of absorbance at 254 nm.

F. CMF-1 May Derive From a Mevalonate Precursor

To address the possibility that CMF-1 is an isoprenoid, it was attempted to block production of CMF-1 in response to agonists by blocking the rate limiting enzyme in isoprenoid synthesis, HMGCoA reductase. A competitive inhibitor of the enzyme, lovastatin (40 ng/ml), was added to the cells to block enzyme activity. Then, to deplete the cells of any CMF-1 precursors that had passed this early step in the synthesis pathway, C5a ($10^{-8}$M) was added. C5a transiently activates cells without leaving them refractory to subsequent stimulation by PMA (11). Lovastatin-treated cells, briefly pulsed with C5a, were then activated with PMA to see if PMA could cause production of CMF-1 despite the block in isoprenoid production.

PMA could not increase rosetting in the blocked cells, but could when the block was overcome by adding mevalonate, the product of HMGCoA reductase, to the media (Table 11). This experiment supports the possibility that CMF-1 is a downstream product of the mevalonate synthesis pathway.

TABLES

TABLE 1

Lipids extracted from activated PMN modulate the CR3 activity of unstimulated PMN.

| stimulus | binding of EC3bi (AI) |
|---|---|
| none | 103 |
| lipids from stimulated PMN | 439 |
| lipids from resting PMN | 122 |
| GM2 | 139 |
| GD1a | 141 |
| GT1b | 156 |
| PMA, 20' | 589 |

A variety of substances were applied to resting adherent human PMN for 45 minutes at 37° C. Cells were then washed and allowed to bind to -erythrocytes coated with C3bi (EC3bi) for 15 minutes at 37° C. The attachment index is the number of erythrocytes bound per 100 phagocytes. Untreated resting PMN give low background binding levels in this rosetting assay. The gangliosides were applied at 100 µg/ml. Phorbol myristate acetate (PMA) was at 30 ng/ml. Partially purified lipids from PMA-activated PMN were applied at 32 u/ml. The extract from resting PMN derived from 10-fold more cells than the extract from activated PMN.

TABLE 2

Rosetting induced by CMF-1 is inhibitable by antibodies against CR3 and C3bi.

| stimulus | antibody | binding of EC3bi (AI) |
|---|---|---|
| none | none | 16 |
| CMF-1 | none | 206 |
| CMF-1 | IB4 | 83 |
| CMF-1 | C39 | 31 |
| CMF-1 | OKM10 | 27 |
| CMF-1 | OKM1 | 175 |

Partially purified CMF-1 at 42 units/ml was added to PMN in the CMF-1 assay in the presence or absence of various monoclonal antibodies. IB4 recognizes CD18, OKM10 and OKM1 recognize CD11b. C39 is against the C3 molecule. Antibodies were used at a final concentration of 10 µg/ml. This experiment is representative of three repeats.

TABLE 3

CMF-1 production correlates with CR3 binding activity.

| | units extractable per $10^7$ cells |
|---|---|
| lipids from untreated cells | <0.33 |
| lipids from cells in PMA, 20' | 2 |
| lipids from cells in PMA, 60' | 0.5 |

Partially purified lipids from cells treated for 0, 20 or 60 minutes with PMA were tested for CMF-1 activity in the rosetting assay.

TABLE 4

| CMF-1 activity is not due to extracted platelet activating factor. | | |
|---|---|---|
| stimulus | inhibitor | binding of EC3bi (AI) |
| none | none | 112 |
| PAF, 100 nM | none | 370 |
| PAF, 100 nM | WEB 2086 | 106 |
| PAF, 1 nM | none | 312 |
| PAF, 1 nM | WEB 2086 | 169 |
| CMF-1 | none | 652 |
| CMF-1 | WEB 2086 | 575 |

CMF-1 (42 u/ml, partially purified from fNLLP treated cells) or platelet activating factor (PAF) was tested in the rosetting assay in the presence or absence of WEB2086 (10 μM), a PAF receptor antagonist. The CMF-1 used here was partially purified from cells treated with fNLLP for 5 minutes at 37° C. This experiment is representative of three repeats.

TABLE 5

| CMF-1 increases binding of both C3bi- and lipid IVa-coated particles to CR3. | | |
|---|---|---|
| binding (AI) of stimulus | EC3bi | EIVa |
| none | 57 | 13 |
| CMF-1, 42 u/ml | 650 | 117 |

PMN were incubated in the presence or absence of CMF-1 (from fNLLP treated cells, 42 u/ml) for 15 minutes, 37° C. Cells were washed and incubated with C3bi-coated or lipid IVa-coated sheep erythrocytes for 15 minutes, 37° C. This experiment is representative of three repeats.

TABLE 6

| CMF-1-induced binding of PMN to fibrinogen is CD18-dependent. | | |
|---|---|---|
| stimulus | antibody | # cells per mm² |
| none | none | 200 ± 120 |
| CMF-1 | none | 680 ± 170 |
| CMF-1 | IB4 | 220 ± 140 |
| CMF-1 | W632 | 560 ± 220 |
| PMA | none | 1130 ± 230 |
| PMA | IB4 | 130 ± 50 |
| PMA | W632 | 880 ± 120 |

PMN were allowed to adhere to fibrinogen-coated plastic surfaces in the presence or absence of agonists and mAbs. CMF-1 was applied at 42 u/ml, PMA at 30 ng/ml and Abs at 10 μg/ml. IB4 recognizes CD18, while W632 recognizes class I MHC molecules. These antigens are present on the PMN surface in approximately equal numbers. Cells are applied to surfaces in the presence of Ab for 30 minutes, 0 C and then agonists are added and binding is allowed to occur for 30 minutes, 37° C. Cells remaining bound after a wash step are scored by phase-contrast microscopy. Data is the average of two experiments, two wells each.

TABLE 7

| CD18-associated lipids have CMF-1 activity. | |
|---|---|
| stimulus | binding of EC3bi (AI) |
| none | 25 |
| CD18 assoc lipids, PMN + PMA | 190 |
| sepharose assoc lipids, PMN + PMA | 43 |

Sepharose beads conjugated to the anti-CD18 mAb, IB4, were used to immunoprecipitate CR3. Beads were mixed with an octyl glucoside lysate (25 mM) of $3 \times 10^8$ PMN treated with PMA for 20 minutes. Detergent was washed away from the beads and CD18-associated lipids were extracted with chloroform:methanol=2:1. This extract was assessed for CMF-1 activity in the rosetting assay. Sepharose beads lacking antibody were also extracted as a control.

TABLE 8

| None of the following have CMF-1 activity in the rosetting assay. | |
|---|---|
| at 100 μg/ml: | at 50, 5 and 0.5 μg/ml: |
| GM1, asialo GM1 | GQ1b |
| GM2, asialo GM2 | PC, PC dimyr |
| GM3 | myristic anhydride |
| GD1a, GD1b | phosphatidic acid: |
| GD2, GD3 | dilauroyl, dimyristoyl, |
| GT1b | dioleoyl |
| lactosylceramide | lysophosphatidic acid |
| globoside | myoinositol bis phosphate |
| sulfatide | lysophosphatidylinositol |
| bovine brain gangliosides | dimyristoyl phosphatidyl glycerol |
| | dolichol monophosphate |

TABLE 9

| CMF-1 activity is unaffected by a variety of chemical and enzymatic treatments. |
|---|
| 30% NH₃OH:CH₃OH = 1:1, room temperature, overnight |
| 1 N NaOH, 75° C., 3 hours |
| acetic anhydride:glacial acetic acid = 2:3, 150° C., 48 hours |
| 1 N acetic acid, 100° C., 45' |
| V. cholera neuraminidase, 0.1 U/ml, 37° C., overnight |
| 2 N methanolic HCl, 75° C., 5 hours |
| 0.5 N methanolic HCl, 100° C., 2 hours |
| 50% HF, 48 hours, 0° C. |
| bacterial alkaline phosphatase, 0.04 U/ml, 37° C., overnight |
| proteinase K, 1.6 mU/ml, 37° C., overnight |
| 0.5M NaBH₄ in 3M NaOH, room temperature, overnight |
| 2 mM NaIO₄ in 70% ethanol, room temperature, overnight |
| 30% H₂O₂ in 10 μM FeSO₄, room temperature, overnight |
| 0.25M nitrous acid in 0.1M acetate buffer, pH 3.8, 8 hours, room temperature |

Partially purified CMF-1 was subjected to these modifications in an attemp to discover the nature of the active molecule. In all cases, a sensitive lipid substrate, either dilinoleoyl phosphatidylcholine or ganglioside GM1, were treated in parallel. Destruction of the control molecule was monitored by thin layer chromatography. CMF-1 activity was tested before and after treatment by rosetting assay. Where necessary, CMF-1 was purified away from enzyme or salts after the reaction by a butanol:water=1:1 extraction. CMF-1 partitions to the butanol phase.

TABLE 10

| Ozonolysis destroys CMF-1 activity. | |
|---|---|
| stimulus | binding of EC3bi (AI) |
| none | 139 |
| PMA | 1000 |
| partially purified CMF-1, 7 u/ml | 445 |
| purified CMF-1, 7 u/ml | 500 |
| purified CMF-1, + O₃, 21 u/ml | 95 |

50 units of CMF-1 were purified by size exclusion chromatography (see FIG. 16) and resuspended in ethyl acetate. Ozone (2 ppm) was bubbled through the solution for 15 minutes at room temperature. CMF-1 activity was assayed against starting material by rosetting assay.

TABLE 11

| CMF-1 is a product of the mevalonate pathway. | | |
|---|---|---|
| | attachment index | |
| stimulus | experiment 1 | experiment 2 |
| resting PMN | 32 | 19 |
| lovastatin | 48 | ND |
| lovastatin + C5a | 86 | 37 |

TABLE 11-continued

CMF-1 is a product of the mevalonate pathway.

| stimulus | attachment index | |
|---|---|---|
| | experiment 1 | experiment 2 |
| PMA | 362 | 253 |
| C5a + PMA | ND | 309 |
| lovastatin + C5a + PMA | 74 | 50 |
| lovastatin, mevalonate, C5a + PMA | 465 | 281 |
| CMF-1 | 511 | 277 |
| lovastatin + CMF-1 | 372 | 261 |
| lovastatin, C5a + CMF-1 | 302 | 279 |

PMN ($2 \times 10^6$ per ml) were added to wells for a rosetting assay and then treated with lovastatin (40 μg/ml) with or without mevalonate (0.2 μg/ml) for 60 minutes at 37° C.

In some wells, C5a ($10^{-8}$M) was added after the first 15 minutes. CMF-1 (42 u/ml) or PMA (30ng/ml) were added for 15 minutes and then EC3bi were added for another 15 minutes. EIgG were added to a set of wells as a control, and their binding was found to be unaffected by any combination of additives to the well (data not shown). These data are two representative experiments of four repeats.

REFERENCES

1. Hynes RO. Integrins: A family of cell surface receptors. Cell 48:549–554, 1987.
2. Wright SD, SK Lo and PA Detmers. Specificity and regulation of CD18-dependent adhesions, in *Leukocyte Adhesion Molecules*, TA Springer, DC Anderson, AS Rosenthal and R Rothlein, eds. New York: Springer Verlag, 1990, pp.190–207.
3. Tuomanen EI, K Saukkonen, S Sande, C Cioffe and SD Wright. Reduction of inflammation, tissue damage, and mortality in bacterial meningitis in rabbits treated with monoclonal antibodies against adhesion-promoting receptors of leukocytes. J Exp Med 170:959–968, 1989.
4. Simpson PJ, RF Todd III, JC Fantone, JK Mickelson, JD Griffin, BR Luccesi, MD Adams, P Hoff, K Lee and CE Rogers. Reduction of experimental canine myocardial reperfusion injury by a monoclonal antibody (anti-Mol, anti-CD11b) that inhibits leukocyte adhesion. J Clin Invest 81:624–629,1988.
5. Vedder NB, RK Winn, CL Rice, EY Chi, K-E Arfors and JM Harlan. A monoclonal antibody to the adherence-promoting leukocyte glycoprotein, CD18, reduces organ injury and improves survival from hemorrhagic shock and resuscitation in rabbits. J Clin Invest 81:939–944, 1988.
6. Hernandez LA, MB Grisham, B Twohig, K-E Arfors, JM Harlan and DN Granger. Role of neutrophils in ischemia-reperfusion-induced microvascular injury. Am J Physiol 253:H699–H703,1987.
7. Wright SD and MTC Jong. Adhesion-promoting receptors on human macrophages recognize *E. coli* by binding lipopolysaccharide. J Exp Med 164:1867–1888, 1986.
8. Wright SD, SM Levin, MTC Jong, Z Chad, and LG Kabbash. CR3 (CD11b/CD18) expresses one binding site for Arg-Gly-Asp-containing peptides, and a second site for bacterial lipopolysaccharide. J Exp Med 169:175–183, 1989.
9. Wright SD and BC Meyer. Phorbol esters cause sequential activation and deactivation of complement receptors on polymorphonuclear leukocytes. J Immunol 20 136:1759–1764, 1986.
10. Lo SK, GA Van Seventer, SM Levin and SD Wright. Two leukocyte receptors (CD11a/CD18 and CD11b/CD18) mediate transient adhesion to endothelium by binding to different ligands. J Immunol 143:3325–3329,1989.
11. Lo SK, PA Detmers, SM Levin and SD Wright. Transient adhesion of neutrophils to endothelium. J Exp Med 169:1779–1793, 1989.
12. Detmers PA, SD Wright, E Olsen, B Kimball and Z Cohn. Aggregation of complement receptors on human neutrophils in the absence of ligand. J Cell Biol 105:1137–1145, 1987.
13. Baggiolini M, B Dewald and M Thelen. Effects of PAF on neutrophils and mononuclear phagocytes. Prog Biocham Pharmacol 22:90–105, 1988.
14. Patarroyo M, M Jondal, J Gordon and E Klein. Characterization of the phorbol 12,13-dibutyrate induced binding between human lymphocytes. Cell Immunol 81:373–383, 1983.
15. Rothlein R and T Springer. The requirement for lymphocyte function associated antigen 1 in homotypic leukooyte adhesion stimulated by phorbol ester. J Exp Med 163:1132–1149, 1986.
16. Wright SD and SC Silverstein. Tumor-promoting phorbol esters stimulate C3b and C3b' receptor-mediated phagocytosis in cultured human monocytes. J Exp Med 156:1149–1164, 1982.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. The Complement Receptor 3 (CR3) modulator, CMF-1, in purified form, which CR3 modulator can be synthesized by polymorphonuclear leukocytes in response to agonists that enhance the activity of complexes of CD18, is capable of binding directly to said CD18, is an acidic amphiphilic compound, will retain its activity after treatment with strong base, and has a molecular weight of about 340 daltons, as determined by size exclusion chromatography.

2. The CR3 modulator of claim 1 wherein said CR3 modulator derives from a biosynthetic product of mevalonate synthesis and possesses an isoprenoid structure.

3. The CR3 modulator of claims 1 or 2 wherein said CR3 modulator activates the adhesion-promoting ability of CD18, increases the affinity for ligands of the receptor CR3 at the binding site for C3 bi, increases polymorphonuclear leukocyte binding to endothelial cells, fibrinogen-coated substrates and Lipid IVa, and increases LPA-1-mediated lymphocyte adhesion.

4. The CR3 modulator of claim 3 wherein said CR3 modulator does not induce the production of TNF by whole blood, and does not cause the degranulation of polymorphonuclear leukocytes.

5. The CR3 modulator of claim 1 or 2, said CR3 modulator having an isotopic label.

6. A method for preparing the CR3 modulator of claim 1 comprising:
   a) gathering a sample of polymorphonuclear leukocytes from a mammal; and b) isolating said CR3 modulator from said polymorphonuclear leukocytes.

7. A Complement Receptor 3 (CR3) modulator prepared by a method comprising:
   a) extracting lipids from polymorphonuclear leukocytes;
   b) eluting the extracted lipids of step (a) that are anionic lipids from an anion exchange column;
   c) eluting the anionic lipids from a reverse phase chromatography column, wherein said CR3 modulator elutes at 50-55% acetonitrile in a gradient of water to acetonitrile of 1% per minute;

which CR3 modulator can be synthesized by polymorphonuclear leukocytes in response to agonists that enhance the activity of complexes of CD18, which is capable of binding directly to said CD18, is an acidic amphiphilic compound, will retain its activity after treatment with strong base, and has a molecular weight of about 340 daltons, as determined by size exclusion chromatography.

8. The CR3 modulator of claim 7, in which the method of preparation further comprises the step of desalting the anionic lipids eluted in step (b).

9. The CR3 modulator of claim 7 or 8, in which the method of preparation further comprises a step of partitioning the anionic lipids in an aqueous phase of a two phase system, which two phase system consists of an organic solvent and an aqueous solvent.

10. The CR3 modulator of claim 1 or claim 7 which is characterized by an ultraviolet (UV) spectrum having a maximum at 196 nm with a slight shoulder out to 300 nm.

11. The CR3 modulator of claim 1 or 7 which is further characterized by one or more of the following properties: it is not reactive with acetic anhydride; it is not affected by desialylation with acetic acid or by neuraminidase; it is not destroyed by acid hydrolysis; it is unaffected by phosphatase or protease treatment; and it is not affected by reduction with sodium borohydride, oxidation with hydrogen peroxide, or oxidation with periodate.

12. The CR3 modulator of claim 1 or claim 7 which is capable of being destroyed by ozonolysis.

13. The CR3 modulator of claim 1 or claim 7 which will partition to an aqueous phase in a Folch partition.

14. A composition comprising the CR3 modulator of claim 1 or claim 7.

15. The composition of claim 14 in which the CR3 modulator is present in a micellar complex having an apparent molecular weight of greater than approximately 2,000 daltons, as determined by size exclusion chromatography.

16. The composition of claim 15 which further comprises phosphatidylcholine.

* * * * *